(12) United States Patent
Uhlig et al.

(10) Patent No.: US 11,959,140 B2
(45) Date of Patent: Apr. 16, 2024

(54) METHOD FOR MONITORING METABOLISM BEFORE AND AFTER EXERCISE OR INJURY USING SALIVARY MICRO-RNAS

(71) Applicants: QUADRANT BIOSCIENCES INC., Syracuse, NY (US); PENN STATE RESEARCH FOUNDATION, University Park, PA (US); THE RESEARCH FOUNDATION FOR THE STATE UNIVERSITY OF NEW YORK, Syracuse, NY (US)

(72) Inventors: Richard Uhlig, Ithaca, NY (US); Steven D. Hicks, Hershey, PA (US); Frank A. Middleton, Fayetteville, NY (US)

(73) Assignees: QUADRANT BIOSCIENCES INC., Syracuse, NY (US); PENN STATE RESEARCH FOUNDATION, University Park, PA (US); THE RESEARCH FOUNDATION FOR THE STATE UNIVERSITY OF NEW YORK, Syracuse, NY (US)

( * ) Notice: Subject to any disclaimer, the term of this patent is extended or adjusted under 35 U.S.C. 154(b) by 0 days.

(21) Appl. No.: 16/975,840

(22) PCT Filed: Feb. 27, 2019

(86) PCT No.: PCT/US2019/019771
§ 371 (c)(1),
(2) Date: Aug. 26, 2020

(87) PCT Pub. No.: WO2019/168933
PCT Pub. Date: Sep. 6, 2019

(65) Prior Publication Data
US 2020/0407795 A1 Dec. 31, 2020

Related U.S. Application Data

(60) Provisional application No. 62/635,729, filed on Feb. 27, 2018.

(51) Int. Cl.
*C12Q 1/6883* (2018.01)

(52) U.S. Cl.
CPC ..... *C12Q 1/6883* (2013.01); *C12Q 2600/178* (2013.01)

(58) Field of Classification Search
CPC ............ C12Q 1/6883; C12Q 2600/178; C12Q 2600/112; C12Q 2600/158
See application file for complete search history.

(56) References Cited

U.S. PATENT DOCUMENTS

2012/0282169 A1 11/2012 Duan et al.
2017/0262581 A1 9/2017 Kozono et al.

FOREIGN PATENT DOCUMENTS

| WO | WO 2013/032962 A2 | 3/2013 |
| WO | WO 2015/074010 A2 | 5/2015 |
| WO | WO 2015/074010 A3 | 5/2015 |
| WO | WO 2017/044650 A1 | 3/2017 |
| WO | WO 2018/005791 A1 | 1/2018 |

OTHER PUBLICATIONS

Steven D. Hicks, et al. "Salivary miRNA profiles identify children with autism spectrum disorder, correlate with adaptive behavior, and implicate ASD candidate genes involved in neurodevelopment" BMC Pediatrics (2016) 16:52 (Year: 2016).*
A. Konstantinidou, et al., "Acute Exercise Alters the Levels of Human Saliva miRNAs Involved in Lipid Metabolism", Int J Sports Med 2016; 37(07): 584-588 (Year: 2016).*
Vivian G. Cheung, et al. "Natural variation in human gene expression assessed in lymphoblastoid cells" Nat Genet Mar. 2003;33(3):422-5. (Year: 2003).*
Konstantinidou (Int J Sports Med 2016; 37(07): 584-588).*
Silva (Progress in Cardiovascular Disease 60 (2017) vol. 130-151).*
International Search Report and Written Opinion dated Jul. 1, 2019 in PCT/US2019/019771 filed on Feb. 27, 2019.
Poulsen, D. et al., "Thymosin Beta-4 Treatment Alters Specific Plasma miRNA Following Severe TBI," Poster #: 41906, Feb. 6, 2018, https://aans.multilearning.com/util/document_library?g_id= 274&dc_id=4280, pp. 1-9, total pages.

* cited by examiner

*Primary Examiner* — Amanda Haney
(74) *Attorney, Agent, or Firm* — Oblon, McClelland, Maier & Neustadt, L.L.P.

(57) ABSTRACT

A method for evaluating or monitoring metabolic effects of exercise or injury by detecting and/or quantifying microRNAs in saliva. Compositions and methods of treatment based on detection of microRNAs.

8 Claims, 7 Drawing Sheets

Scores Plot

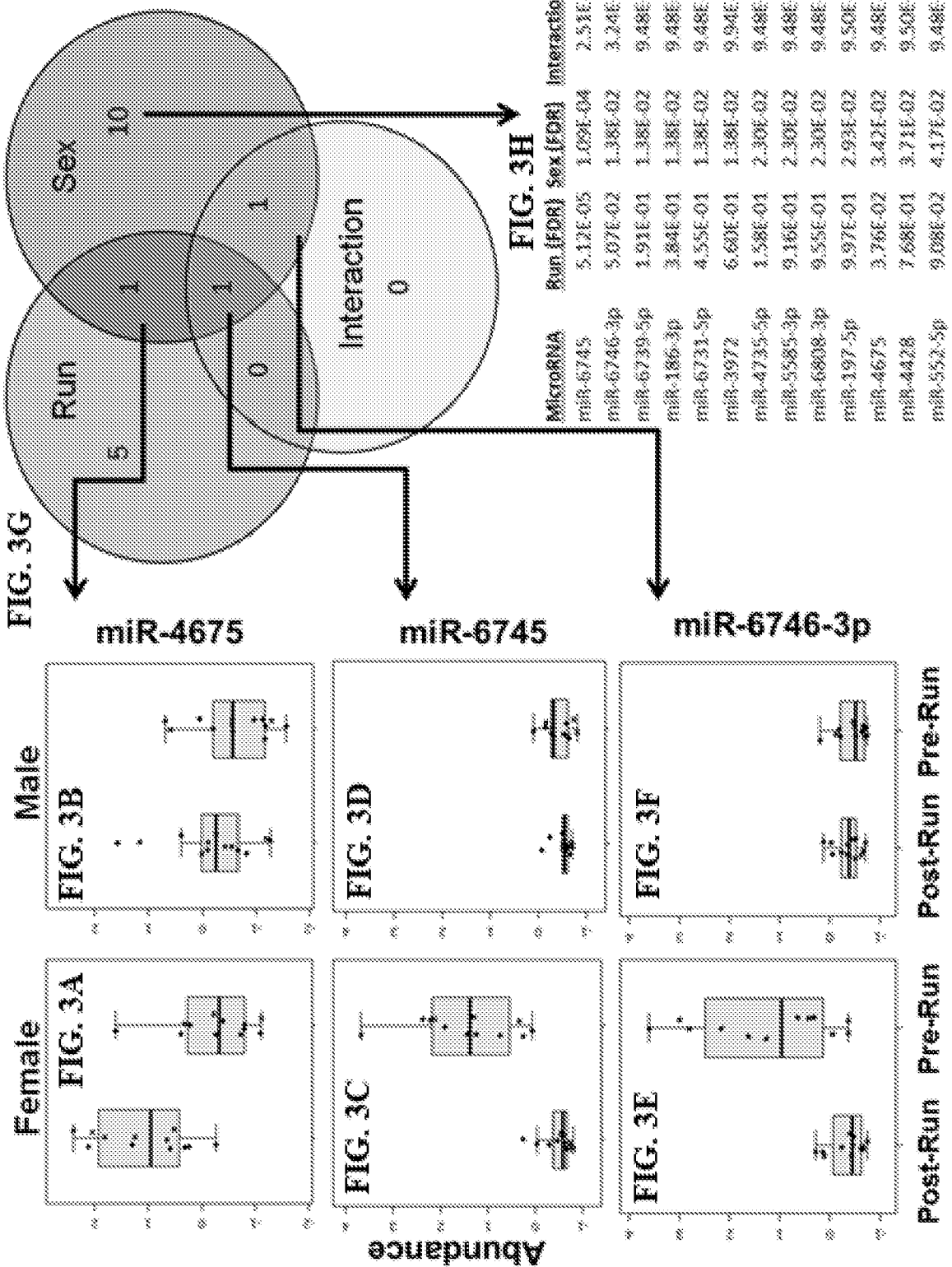

METHOD FOR MONITORING METABOLISM BEFORE AND AFTER EXERCISE OR INJURY USING SALIVARY MICRO-RNAS

CROSS-REFERENCE TO RELATED APPLICATIONS

This provisional application incorporates by reference the contents of U.S. Provisional Application Nos. 62/475,705, filed Mar. 23, 2017 entitled METHOD OF NORMALIZING EPIGENETIC DATA TO ACCOUNT FOR TEMPORAL VARIATIONS; 62/475,698, filed Mar. 23, 2017 entitled IDENTIFICATION AND CHARACTERIZATION OF TRAUMATIC BRAIN INJURY USING EPIGENETIC BIOMARKERS, U.S. Provisional Application No. 62/480,079, filed Mar. 31, 2017 entitled MOLECULAR AND FUNCTIONAL BIOMARKERS OF MILD TRAUMATIC BRAIN INJURY and U.S. Provisional 62/502,107, filed May 5, 2017 entitled METHOD FOR PREDICTION OF PROLONGED CONCUSSION SYMPTOMS.

STATEMENT REGARDING FEDERALLY SPONSORED RESEARCH OR DEVELOPMENT

This invention was made with government support under Grant No. R42-MH111347-02A1 awarded by the National Institutes of Health. The Government has certain rights in the invention.

BACKGROUND

Field of the Invention

A method for evaluating or monitoring metabolic effects of exercise or injury by detecting and/or quantifying microRNAs in saliva.

Description of Related Art

The "background" description provided herein is for the purpose of generally presenting the context of the disclosure. Work of the presently named inventor(s), to the extent it is described in this background section, as well as aspects of the description which may not otherwise qualify as prior art at the time of filing, are neither expressly or impliedly admitted as prior art against the present invention.

Exercise and miRNA. Micro-ribonucleic acids (miRNAs) are short, non-coding molecules that regulate the translation of coding messenger RNA (mRNA) into proteins; see Fabian, M. R., Sonenberg, N., & Filpowicz, W. (2010). Regulation of mRNA translation and stability by microRNAs. *Annual review of biochemistry*, 79, 351-379. These master regulators are found in cells throughout the human body, and control numerous physiologic processes, including cellular metabolism, repair, and signaling; Rottiers, V., & Näär, A. M. (2012). MicroRNAs in metabolism and metabolic disorders. *Nature reviews Molecular cell biology*, 13(4), 239; Jakob, P., & Landmesser, U. (2011). Role of microRNAs in stem/progenitor cells and cardiovascular repair. *Cardiovascular research*, 93(4), 614-622. In fact, stabilization of miRNAs within extracellular vesicles, or other protein-mediated carriers, allows for transportation through extracellular fluids to distant tissues, where they can dock, cross the cell membrane and influence targeted protein pathways; Dinger, M. E., Mercer, T. R., & Mattick, J. S. (2008). RNAs as extracellular signaling molecules. *Journal of molecular endocrinology*, 40(4), 151-159. These characteristics have garnered miRNAs much attention as potential biomarkers in human health and disease; Michael, A., Bajracharya, S. D., Yuen, P. S., Zhou, H., Star, R. A., Illei, G. G., & Alevizos, I. (2010). Exosomes from human saliva as a source of microRNA biomarkers. *Oral diseases*, 16(1), 34-38.

In healthy human adults miRNAs appear to mediate physiologic adaptations to endurance exercise; Davidsen, P. K., Gallagher, I. J., Hartman, J. W., Tarnopolsky, M. A., Dela, F., Helge, J. W., & Phillips, S. M. (2010). High responders to resistance exercise training demonstrate differential regulation of skeletal muscle microRNA expression. *Journal of applied physiology*, 110(2), 309-317; Eisenberg, I., Alexander, M. S., & Kunkel, L. M. (2009). miRNAS in normal and diseased skeletal muscle. *Journal of cellular and molecular medicine*, 13(1), 2-11. Several muscle-specific miRNAs have been described in adult human tissue, and these miRNAs demonstrate dynamic expression patterns following aerobic exercise; Güller, I., & Russell, A. P. (2010). MicroRNAs in skeletal muscle: their role and regulation in development, disease and function. The Journal of physiology, 588(21), 4075-4087; Nielsen, S., Scheele Yfanti, C., Åkerström, T., Nielsen, A. R., Pedersen, B. K. and Laye, M., 2010. Muscle specific microRNAs are regulated by endurance exercise in human skeletal muscle. The Journal of physiology, 588(20), pp. 4029-4037.

Interestingly, muscle-specific and muscle-related miRNAs can also be measured in circulating plasma following exercise. A longitudinal study of plasma-based miRNAs in 10 male rowers found that a subset of miRNAs underwent dynamic regulation following sustained aerobic activity, and that these miRNAs targeted mRNAs involved in skeletal and cardiac muscle contractility; Baggish, A. L., Hale, A., Weiner, R. B., Lewis, G. D., Systrom, D., Wang, F., . . . & Chan, S. Y. (2011). Dynamic regulation of circulating microRNA during acute exhaustive exercise and sustained aerobic exercise training. *The Journal of physiology*, 589 (16), 3983-3994. One muscle-specific miRNA, miR-133a, has demonstrated exercise-related changes in multiple studies. In these studies, involving primarily male athletes, miR-133a changes depended on the selected exercise activity, and were most increased by eccentric exercise regimens; Uhlemann, M., Möbius-Winkler, S., Fikenzer, S., Adam, J., Redlich, M., Möhlenkamp, S., . . . & Adams, V. (2014), Circulating microRNA-1.26 increases after different forms of endurance exercise in healthy adults. *European journal preventative cardiology*, 21(4), 484-491. Banzet, S., Chennaoui, M., Girard, O., Racinais, S., Drogou, C., Chalabi, H., & Koulmann, N. (2013). Changes in circulating microRNAs levels with exercise modality. *Journal of applied physiology*, 115(9), 1237-1244. Another investigation of 14 male distance runners showed that circulating miRNA levels correlated with aerobic performance parameters such as maximum oxygen uptake and individual lactate threshold. Thus miRNAs may serve as markers of exercise capacity; Mooren, F. C., Viereck, J., Krüger, K., & Thum, T. (2013). Circulating microRNAs as potential biomarkers of aerobic exercise capacity. *America Journal of Physiology-Heart and Circulatory Physiology*, 306(4), H557-H563. Though the majority of exercise studies have focused on blood-based miRNA levels and muscle-related targets, a study by Konstantinidou and colleagues (2015) examined eight salivary miRNAs and identified two that were altered after stationary bike exercise. These miRNAs targeted genes involved lipid metabolism; Konstantinidou, A., Mougios, V., &. Sidossis. L. S. (2016). Acute Exercise Alters the Levels of Human Saliva miRNAs Involved in Lipid Metabolism. *International journal of sports medicine*, 37(07), 584-588.

The importance of understanding salivary miRNA dynamics in exercise is underscored by two recent studies that showed specific saliva miRNAs may be used to identify the presence of concussion and predict the duration of concussion symptoms in children; Hicks, S. D., Johnson, J., Carney, M. C. Bramley, H., Olympia, R. P., Loeffert, A. C., &. Thomas. N. J. (2018), Overlapping microRNA expression in saliva and cerebrospinal fluid accurately identifies pediatric traumatic brain injury. *Journal of neurotrauma*, 35(1), 64-72; Johnson, J. J., Loeffert, A. C., Stokes, J., Olympia, R. P., Bramley, H., &. Hicks, S. D. (2018). Association of salivary microRNA changes with prolonged concussion symptoms. *JAMA pediatrics*. Considering the number of youth concussions that occur during athletic participation, identifying the saliva miRNAs that may be confounded by recent aerobic activity could be critical for accurate biomarker development.

In addition, previous investigations of miRNA levels in exercise have focused almost exclusively on male participants, despite the fact that females display unique musculoskeletal, cardiovascular, and metabolic responses to aerobic training; Magkos, F., Kavouras, S. A., Yannakoulia, Karipidou, M., Sidossi, S., & Sidossis, L. S. (2007). The bone response to non-weight-bearing exercise is sport-, site-, and sex-specific. *Clinical Journal of Sport Medicine*, 17(2), 123-128; Blumenthal, J. A., Emery, C. F., Madden, D. J., George, L. K., Coleman, R. E., Riddle, M. W., . . . & Williams, R. S. (1989). Cardiovascular and behavioral effects of aerobic exercise training in healthy older men and women. *Journal of gerontology*, 44(5), M147-M157; Tarnopolsky, M, A. (2000). Gender differences in substrate metabolism during endurance exercise. *Canadian Journal of Applied Physiology*, 25(4), 312-327. Previous studies of miRNAs in exercise participants have also used hypothesis-driven approaches, focusing on 5-20 miRNAs at the exclusion of more than 2,000 known miRNA candidates. None of these investigations have confirmed downstream impacts of miRNA changes on gene targets.

In view of the above, the inventors sought to address these gaps in the scientific literature by using a high throughput sequencing technique to investigate salivary changes in global RNA expression (miRNA and mRNA) following aerobic running participation by male and female collegiate distance runners. The investigated whether numerous salivary miRNAs underwent exercise-related changes in expression and whether these miRNAs will targeted a diverse array of mRNA targets involved in metabolic, hemodynamic, and muscle-related adaptations to endurance running.

The inventors conducted a large and comprehensive study of the human microRNA responses to aerobic exercise that interrogates the entire microtranscriptome. This work identified select microRNAs that change in human saliva following long-distance running. These microRNAs target various mRNA targets downstream form parts of regulatory networks involving multiple physiologic processes related to metabolism and fluid balance. The inventors also identified unique changes in miRNA in female athletes which appear to underlie distinct metabolic responses to endurance training.

Concussion and mTBI. The inventors also investigated miRNA levels associated with exercise and/or injury, such as concussion or mTBI.

Three million concussions occur in the United States each year many resulting in mild traumatic brain injury ("mTBI"), Concussion, also known as mild traumatic brain injury (mTBI) is typically defined as a head injury with a temporary loss of brain function; *Traumatic Brain Injury (TBI): Condition Information*". NICHD, https://_www.nichd.nih.gov/health/topics/tbi/conditioninfo/default (last accessed Jan. 25, 2018). Symptoms may include headache, trouble with thinking, memory, or concentration, nausea, blurry vision, sleep disturbances, or mood changes; some symptoms may begin immediately, while other may appear days after the injury; NICHD, https://_www.nichd.nih.gov/health/topics/tbi/conditioninfo/symptoms (last accessed Jan. 25, 2018; incorporated by reference). Fewer than 10% of sports-related concussions among children are associated with loss of consciousness; Halstead, M E; Walter, K D; Council on Sports Medicine and, Fitness. (September 2010). *Academy of Pediatrics. Clinical report—sport-related concussion in children and adolescents*". Pediatrics. 126 (3): 597-615. doi:10. 1542/peds.2010-2005. PMID 20805152. It is not unusual for symptoms to last up to four weeks; Mahooti, N (January 2018). *Sports-Related Concussion: Acute Management and Chronic Post-concussive Issues*. Child and adolescent psychiatric clinics of North America. 27 (1): 93-108. doi:10.1016/j.chc.2017.08.005. PMID 29157505.

Common causes of concussion include motor vehicle collisions, falls, sports injuries, and bicycle accidents. Up to five percent of sports injuries are concussions. The U.S. Centers for Disease Control and Prevention estimates that 300,000 sports-related concussions occur yearly in the U.S., but that number includes only athletes who lost consciousness. Since loss of consciousness is thought to occur in less than 10% of concussions, the CDC estimate is likely lower than the real number. Sports in which concussion is particularly common include football and boxing (a boxer aims to "knock out", i.e. give a mild traumatic brain injury to, the opponent). Another preventable cause of TBI is shaken baby syndrome (SBS). The syndrome can occur when an infant is shaken violently or hit. The mechanism may involve either a direct blow to the head or forces elsewhere on the body that are transmitted to the head. Diagnosis requires less than 30 minutes of loss of consciousness, memory loss of less than 24 hours, and a Glasgow coma scale score of 13 to 15. Otherwise it is considered a moderate or severe traumatic brain injury.

A mTBI is defined as a traumatic disruption of brain function that manifests as altered mental status, loss of consciousness (<20 minutes), or amnesia (<24 hours), with an initial Glasgow Coma Scale score of ≥13 and lack of focal neurological deficits. Concussion symptoms often resolve within two weeks, but some patients will experience cognitive, somatic, emotional, and behavioral symptoms that extend past this period. Those individuals with symptoms lasting longer than 28 days can be classified as having post-concussion syndrome ("PCS").

While most physicians feel capable of diagnosing a concussion, a lack of knowledge about objective factors that permit accurate characterization and prognosis of concussion, mTBIs and TBIs and distinguish them from other can delay specialist referral and execution of an individualized treatment plan. The 2012 Consensus Statement on Concussion in Sport recommended that age-appropriate symptom checklists be administered to children, parents, teachers, and caregivers for accurate clinical assessment of concussions. However, the feasibility of administering and scoring multiple age-specific questionnaires within the time constraints of a typical clinical encounter has prevented physicians from adopting a common concussion evaluation tool. Instead, many investigators have begun to explore alternative diagnostic approaches to concussions.

Research into the use of protein biomarkers as a means of diagnosing, monitoring, and predicting the course of concussions has increased markedly over the past decade. One of the most extensively examined biomarkers has been S100β, a low molecular weight protein expressed in astrocytes and found at low levels in cerebrospinal fluid (CSF) and serum. Levels of S100β correlate with head computed tomography (CT) findings after mTBI in adults, but there are conflicting reports regarding its accuracy in pediatric head trauma. S100β is also produced outside the central nervous system (CNS) and is influenced by disease states, including bone fractures and intra-abdominal injury. These factors give it poor specificity as an mTBI diagnostic test. In addition, S100β is influenced by exercise, limiting its utility in sports-concussions, a common mechanism in adolescents.

Regardless of age, most of the protein biomarkers currently being studied have a low sensitivity for detecting mTBI in individuals who do not have a detectible intracranial lesion. There have also been no protein biomarkers that have reliably been able to predict PCS after a mTBI.

MicroRNAs or miRNAs are considered post-transcriptional gene regulators enabling translational repression, mRNA degradation and gene silencing thus playing a major role in gene expression. They bind on their target usually by partial or complete base pairing on specific miRNA recognition elements (MREs) on mRNA as well as other non-coding RNA sequences such as lncRNAs. Micro ribonucleic acids (miRNAs) are small, endogenous, non-coding molecules that influence protein translation throughout the human body. They are transported through the extracellular space by protective exosomes and micro-vesicles, or bound to proteins, which allows them to be easily detected in serum, CSF, or saliva. Levels of tissue-specific mRNAs released by damaged cells may act as biomarkers of a human disease. Due to their abundance, stability at fluctuating pH levels, resistance to enzymatic degradation, and essential role in transcriptional regulation, miRNAs make ideal biomarker candidates. Some previous studies have examined the utility of miRNAs biomarkers in human TBIs. For example, Pasinetti and colleagues found one miRNA (miR-671-5p) to be decreased in peripheral blood mononuclear cells of nine military veterans with comorbid post-traumatic stress disorder (PTSD) and mTBI compared with nine control veterans with PTSD only; and Redell and colleagues found that of the 108 miRNAs identified in the plasma of age-, gender-, and race-matched controls, 52 were "altered" in 10 subjects after a severe TBI (sTBI); see Pasinetti, G. M., Ho, L., Dooley, C., Abbi, B., & Lange, G. (2012). *Select non-coding RNA in blood components provide novel clinically accessible biological surrogates for improved identification of traumatic brain injury in OEF/OIF Veterans*. American J Neurodegen Dis, 1(1), 88; Redell, J. B., Moore, A. N., Ward III, N. H., Hergenroeder, G. W., & Dash, P. K. (2010). *Human traumatic brain injury alters plasma microRNA levels*. Journal of Neurotrauma, 27(12), 2147-2156 (both incorporated by reference). However, there remains a need for sensitive and specific miRNA biomarkers for concussion and TBI, including mTBI and sTBI, that are easily accessible and that can distinguish concussion or TBI from other physiological states.

In view of the above, the inventors investigated levels of different mi-RNAs in saliva before and after exercise as well as their use in combination with miRNA biomarkers for concussion, mTBI and TBI. Biomarkers for exercise also may be used to monitor, tune, or individualize a health, weight loss, exercise, or sports regimen.

BRIEF SUMMARY OF THE INVENTION

Methods of evaluation or monitoring exercise by measuring miRNA levels in saliva. Methods for assessing or diagnosing concussion or other mTBIs by detecting or quantifying miRNAs in saliva.

BRIEF DESCRIPTION OF THE DRAWINGS

FIG. 3A-3F. Individual salivary miRNAs demonstrate sex-specific responses to exercise Levels of three salivary miRNAs were significantly (FDR<0.05) influenced by pre/post-run status and sex (miR-4675), or run-status/sex interactions (miR-6745 and miR-6746-3p) on a 2-way analysis of variance (ANOVA). Whisker box plots of quantile normalized abundance are shown for male (n=13) and female (n=12) participants pre- and post-run.

FIG. 3G. A Venn diagram indicating the number of salivary miRNAs influenced by sex, run-status, or sex/run-status interactions.

FIG. 3H. Two-way ANOVA false-detection rate (FDR) p-values are shown for the 13 salivary miRNAs influenced by participant sex.

DETAILED DESCRIPTION OF THE INVENTION

Figure 1:
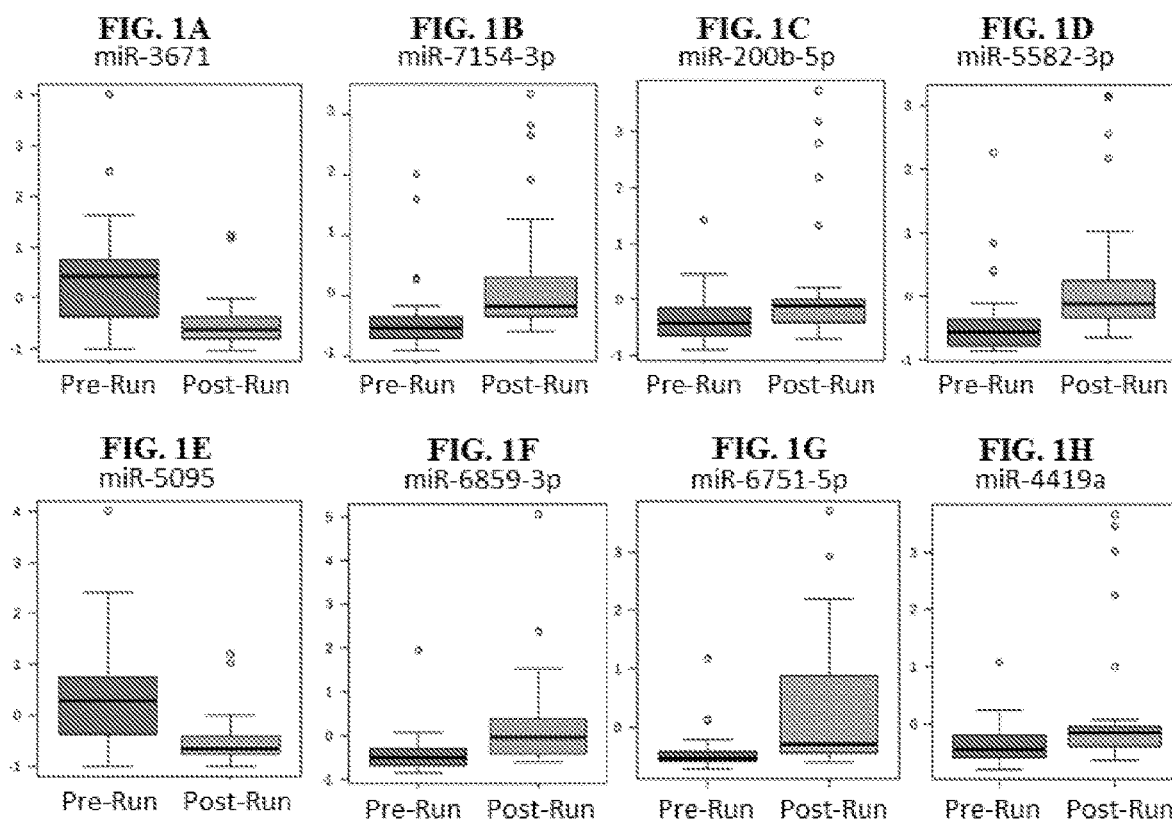
FIGS. 1A-1H. Eight salivary miRNAs demonstrate robust, consistent post-run changes in abundance Whisker box-plots are shown for the eight salivary miRNAs with significant (FDR<0.05) and consistent (>23/25 samples) changes on paired non-parametric Wilcoxon rank-sum testing (n=25). Quantile normalized, mean group expression levels are displayed for pre-run samples (dark grey) and post-run samples (light grey).

Saliva is a slightly alkaline secretion of water, mucin, protein, salts, and often a starch-splitting enzyme (as ptyalin) that is secreted into the mouth by salivary glands, lubricates ingested food, and often begins the breakdown of starches. Saliva is released by the submandibular gland, parotid gland, and/or sublingual glands and saliva release may be stimulated by the sympathetic and/or parasympathetic nervous system activity. Saliva released primarily by sympathetic or parasympathetic induction may be used to isolate microRNAs.

Saliva may be collected by expectoration, swabbing the mouth, passive drool, or by other methods known in the art. It may be collected from the mouth prior to or after a rinse. For example, in some embodiments it may be collected without rinsing the mouth first and in other embodiments after rinsing accumulated saliva out of the mouth and collecting newly secreted saliva, optionally after the administration of a sialogogue, such as a parasympathomimetic drug (e.g., pilocarpine), which acts on parasympathetic muscarinic receptors such as the M3 receptor to induce an increased saliva flow, or after administration of malic acid, ascorbic acid, chewing gum or plant or herbal extracts that promote saliva flow. In other embodiments it may be withdrawn from a salivary gland.

In some embodiments, a saliva sample may be further purified, for example, by centrifugation or filtration. For example, it may be filtered through a 0.22 micron or 0.45 micron membrane and the separated components used to recover microRNAs. In some embodiments, proteins or enzymes that degrade or inhibit detection of microRNA may be removed, inactivated or neutralized in a saliva sample.

microRNA or miRNA is a small non-coding RNA molecule containing about 22 nucleotides, which is found in plants, animals and some viruses, that functions in RNA silencing and post-transcriptional regulation of gene expression; see *Ambros, V* (Sep. 16, 2004). *The functions of animal microRNAs. Nature.* 431 (7006): 350-5. doi:10.1038/nature02871. PMID 15372042; or Bartel, D P (Jan. 23, 2004). *MicroRNAs: genomics, biogenesis, mechanism, and function. Cell.* 116 (2): 281-97. doi:10.1016/S0092-8674(04) 00045-5. *PMID* 14744438, both of which are incorporated by reference. miRNAs are considered post-transcriptional gene regulators enabling translational repression, mRNA degradation and gene silencing thus playing a major role in gene expression. They bind on their target usually by partial or complete base pairing on specific miRNA recognition elements (MREs) on mRNA as well as other non-coding RNA sequences such as lncRNAs.

A miRNA standard nomenclature system uses the prefix "miR" followed by a dash and a number, the latter often indicating order of naming. For example, miR-120 was named and likely discovered prior to miR-241. A capitalized "miR-" refers to the mature form of the miRNA, while the uncapitalized "mir-" refers to the pre-miRNA and the pri-miRNA, and "MIR" refers to the gene that encodes them.

miRNA isolation from biological samples such as saliva and their analysis may be performed by methods known in the art, including the methods described by Yoshizawa, et al., *Salivary MicroRNAs and Oral Cancer Detection*, Methods Mol Biol. 2013; 936: 313-324; doi: 10.1007/978-1-62703-083-0 (incorporated by reference) or by using commercially available kits, such as mirVana™ miRNA Isolation Kit which is incorporated by reference to the literature available at https://_tools.thermofisher.com/content/sfs/manuals/fm_1560.pdf (last accessed Jan. 9, 2018).

Statistical analysis may be performed using Metaboanalyst online software as described at http://_www.metaboanalyst.ca/ (last accessed Jan. 25, 2018).

DIANA-mirPath is a miRNA pathway analysis webserver, providing accurate statistics, while being able to accommodate advanced pipelines. mirPath can utilize predicted miRNA targets (in CDS or 3'-UTR regions) provided by the DIANA-microT-CDS algorithm or even experimentally validated miRNA interactions derived from DIANA-TarBase. These interactions (predicted and/or validated) can be subsequently combined with sophisticated merging and meta-analysis algorithms; see Vlachos, Ioannis S., Konstantinos Zagganas, Maria D. Paraskevopoulou, Georgios Georgakilas, Dimitra Karagkouni, Thanasis Vergoulis, Theodore Dalamagas, and Artemis G. Hatzigeorgiou. *DIANA-mirPath v3. 0: deciphering microRNA function with experimental support.* Nucleic acids research (2015): gkv403 (incorporated by reference) and http://_snf-515788.vm.okeanos.gr-net.gr/ (last accessed Jan. 25, 2018, incorporated by reference.

EXAMPLE

Introduction/Summary. As shown in the Example below and described herein, micro-ribonucleic acids (miRNAs) mediate adaptive responses to endurance exercise. Expression levels of select miRNAs are altered in skeletal muscle, plasma, and saliva following exertion. These alterations can serve as biomarkers of exercise capacity. The work described here utilized high-throughput RNA sequencing to measure changes in salivary RNA expression among 25 collegiate runners following a long-distance run. Alignment to precursor/mature miRNA and mRNA indices permitted interrogation of 4,694 miRNAs and 27,687 mRNAs in pre- and post-run saliva. Pair-wise Wilcoxon rank-sum test identified miRNAs with significant (FDR<0.05) post-run changes. Associations between miRNA levels and predicted mRNA targets were explored with Pearson correlations. Differences between male (n=13) and female (n=12) miRNA responses to running were investigated with a two-way analysis of variance.

Numerous salivary miRNAs changed in response to endurance running and target the expression of genes involved in metabolism, fluid balance, and musculoskeletal adaptations.

There were 122 miRNAs with post-run salivary changes. The eight miRNAs with the largest changes were miR-3671, miR-5095 (down-regulated post-run); and miR-7154-3p, miR-200b-5p, miR-5582-3p, miR-6859-3p, miR-6751-5p, miR-4419a (up-regulated). Predicted mRNA targets for these miRNAs over-represented 15 physiologic processes, including glycerophospholipid metabolism (FDR=0.042), aldosterone-regulated sodium reabsorption (FDR=0.049), and arrhythmogenic ventricular cardiomyopathy (FDR=0.018). Twenty-six miRNA/mRNA pairs had associated changes in post-run salivary levels. Three miRNAs (miR-4675, miR-6745, miR-6746-3p) demonstrated sex-specific responses to exercise. It was also observed that a subset of miRNAs helps differentiate the male and female metabolic responses to prolonged running.

Example 1

Participant Information. An observational cohort design was used to identify changes in salivary RNA among competitive distance runners by comparing pre- and post-run transcript profiles in a pairwise fashion. Participants included 13 male and 12 female collegiate distance runners, ages 18-23 years, who completed their weekly "long run" on the day of the study. "Long run" was defined by a run exceeding 55 minutes and comprising≥20% of weekly running distance. Participant exclusion criteria included acute illness (e.g. upper respiratory infection or gastrointestinal infection), or active orthopedic injury in the past seven days. For all participants, demographic and exercise characteristics were collected through self-reported surveys, including: sex, race/ethnicity, age (years), body mass index (kg/m$^2$), medications, time since last meal (hours), dietary restrictions (presence/absence), average distance run per week (km), run distance on the day of saliva collection (km), run duration (minutes), and run pace (minutes/km).

Saliva and vital signs (including heart rate, body temperature, and blood pressure) were collected approximately 10 minutes before the run, and again 10 minutes after completion of the run. Saliva was collected at these two time-points through expectoration into Oragene RE-100 saliva collection kits (DNA Genotek, Ottawa, Canada) following oral tap-water rinse.

RNA processing/filtering. Saliva samples were stored at -20° C. at the State University of New York Upstate Molecular Analysis Core Facility prior to RNA extraction with a standard Trizol technique and RNeasy mini columns (Qiagen, Valencia California).

The RNA quality and yield for each sample were assessed with an Agilent Bioanalyzer (Agilent Technologies, Santa Clara, California) before completion of library construction and high throughput RNA sequencing.

A NextSeq 500 Instrument (Illumina, San Diego, Calif.) was used to quantify RNA transcripts at a targeted depth of 10 million single end reads per sample and a threshold of 50 base pairs.

Adapter trimming, QC analysis, and RNA read alignment were performed in Partek Flow Software (Partek, St. Louis, Mo.). Reads were aligned to build 38 of the human genome using the Shrimp2 aligner and the Refseq transcripts, miRBase precursor microRNA (version 21), or miRBase mature microRNA (version 21) reference indices.

Alignment parameters for mature and precursor microRNAs included: 100% window length with local, ungapped alignment, and 10 maximum hits per read. Single best mapping was used to align mRNA transcripts, and included a 140% match window length, with a mismatch score of -15, gap open score of -33, and a window overlap filter of 90%. The 27,867 transcripts interrogated by Refseq alignment (including mRNAs, long non-coding RNAs, small nucleolar RNAs, and other non-coding RNA species) were filtered to include only the 8,901 RNAs present in raw counts >10 in at least 20% of samples.

The 4,694 miRNAs interrogated by miRBase alignment (including both mature and precursor miRNAs) were filtered to include only 460 miRNAs: 408 miRNAs were chosen based on their robust salivary expression (present in raw counts of ≥10 per sample in ≥25% of samples), and 52 miRNAs were included because of previous studies indicating they might be influenced by exercise (n=27), or sports-related concussion (n=25); see Baggish, Aaron L. et al. "Dynamic regulation of circulating microRNA during acute exhaustive exercise and sustained aerobic exercise training." *The journal of physiology* 589.16 (2011): 3983-3994; Uhlemann, Madlen, et al. "Circulating microRNA-126 increases after different forms of endurance exercise in healthy adults." European journal of preventive cardiology 21.4 (2014): 484-491; Mooren, Frank C., et al, "Circulating microRNAs as potential biomarkers of aerobic exercise capacity." *American Journal of Physiology-Heart and Circulatory Physiology* 306.4 (2014): H557-H563; Banzet, Sébastien et al. "Changes in circulating microRNAs levels with exercise modality." *Journal of applied physiology* 115.9 (2013). 1237-1244; Aoi, Wataru, et al. "Muscle-enriched microRNA miR-486 decreases in circulation in response to exercise in young men." Frontiers in physiology 4 (2013).

The raw miRNA and mRNA read counts within each sample were separately quantile normalized, mean-centered, and divided by the standard deviation of each variable prior to statistical analysis.

Statistical analysis. The primary outcome of the study was the identification of miRNA features whose concentrations were altered following "long run" completion. Changes in miRNA concentration post-run were determined for the 25 participants using a paired non-parametric Wilcoxon rank-sum test with Benjamini Hochberg false detection rate (FDR) correction. The miRNAs with FDR<0.05 were considered to be significantly altered post-run. A partial least squares discriminant analysis (PLSDA) was used to visualize total miRNA profiles among pre- and post-run samples.

Contributions of individual miRNAs to sample localization on the 2-dimensional PLSDA were quantified with a variable importance in projection (VIP) score.

The 15 miRNAs with the highest VIP score were utilized for hierarchical clustering of pre- and post-run samples with a Pearson distance measure and a complete clustering algorithm. DIANA miRPath (version 3) software was used to interrogate the miRNAs with the most significant post-run changes for predicted mRNA targets.

The mRNAs with moderate target prediction evidence (microT-cds threshold>0.90, p<0.05) were then utilized to identify over-represented KEGG pathways (FDR <0.05) using a Fischer's exact test of conservative EASE score measurement.

Functional influences of post-run miRNA changes on local salivary mRNA expression were interrogated with Wilcoxon rank-sum testing. The salivary mRNAs with nominal post-run expression changes (FDR <0.1) were cross-referenced against predicted mRNA targets of the salivary miRNAs with post-run changes.

Potential interactions among the protein-products for targeted mRNAs were interrogated in String v10 software. Pearson correlation testing was used to identify miRNA-mRNA pairs with associated changes in post-run expression (R≥[0.40]). Pearson testing was also used to investigate participant factors and exercise variables that might influence circulating miRNA levels (R>[0.50]). For correlation testing, permissive p-values (FDR<0.15) were employed to avoid type-II errors in which external influences from participant factors, or exercise variables on miRNA expression might be over-looked.

Finally, a two-way ANOVA was used to explore interactions between participant sex (a factors of interest) with post-run miRNA expression changes. The miRNAs influenced (FDR<0.05) by sex, post-run status, or a sex-run interaction were reported.

Results

Participants. The participants were 48% female (12/25) and 92% Caucasian (23/25) (Table 1). Their mean age was 20 years (±1.3; range 18-23) and mean body mass index was 20.4 (±1.7; range 17.8-23.9). The mean time since last meal was 2.8 hours (±3.3; range 0-10) and 20% (5/25) were fasting (no food/drink in past 8 hours). Twenty percent (5/25) took a prescription medication. Medications included selective serotonin re-uptake inhibitors, oral contraceptives, inhaled beta-agonists, inhaled corticosteroids, and a GABA agonist. Twenty-four percent (6/25) reported dietary restrictions. Average weekly distance run was 89 km/week (±16; range 64-121). On the day of saliva collection, participants ran an average of 18 km (±2.4; range 13-23) at a pace of 4:37/km (±0:22; range 3:59-5:19). The mean run duration was 83 minutes (±13; range 55-120). Pre-run, mean systolic blood pressure for all participants was 117 mmHg (±7; range 108-136) and diastolic pressure was 71 mmHg (±5; range 60-82). Pre-run heart rate was 64 beats/minute (±8; range 44-80) and temperature was 36.7 degrees C. (±0.7; range 34.4-37.7). Post-run, mean systolic pressures increased (p=0.0002) to 126 mm HG (±8; range 110-150) and mean diastolic pressures increased (p=0.0004) to 78 mmHg (±6; range 66-90). Mean post-run heart rate was elevated (p=1.2× $10^{-10}$) to 89 beats/minute (±10; range 75-111), but mean body temperature (36.4 degrees C.±0.9) was not changed (p=0.22). Post-run saliva samples and vital signs were collected, on average, 11 minutes (±3; range 10-20) after run completion.

TABLE 1

Participant Characteristics

| Participant Characteristics | All participants, n = 25 |
|---|---|
| Female, No. (%) | 12 (48) |
| Caucasian, No. (%) | 23 (92) |
| Age in years, mean (SD; range) | 20 (1.3; 18-23) |
| Body mass index in kg/m², mean (SD; range) | 20.4 (1.7; 17.8-23.9) |
| Fasting, No. (%) | 5 (20) |
| Dietary restrictions, No. (%) | 6 (24) |
| Run Characteristics | |
| Average weekly distance in km, mean (SD; range) | 89 (16; 64-121) |
| Run distance in km, mean (SD; range) | 18 (2.4; 13-23) |
| Run duration in minutes, mean (SD; range) | 83 (13; 55-120) |
| Run pace in minutes/km, mean (SD; range) | 4:37 (0:22; 3:59-5:19) |
| Vital Signs | |
| Pre-run heart rate in beats/minute, mean (SD; range) | 64 (8; 44-80) |
| Pre-run body temperature in ° C., mean (SD; range) | 36.7 (0.7; 34.4-37.7) |
| Pre-run systolic blood pressure in mmHg, mean (SD; range) | 117 (7; 108-136) |
| Pre-run diastolic blood pressure in mmHg, mean (SD; range) | 71 (5; 60-82) |
| Post-run heart rate in beats/minute, mean (SD; range) | 89 (10; 75-111) |
| Post-run body temperature in ° C., mean (SD; range) | 36.4 (0.9; 34.7-37.9) |
| Post-run systolic blood pressure in mmHg, mean (SD; range) | 126 (8; 110-150) |
| Post-run diastolic blood pressure in mmHg, mean (SD; range) | 78 (6; 66-90) |
| Time of post-run collection in minutes, mean (SD; range) | 11 (3; 10-20) |

Total miRNA expression. There were a total of 1.24× $10^7$ raw miRNA read counts among the 50 saliva samples. The mean miRNA read count per sample was 2.5×$10^5$ (±2.1×$10^5$; range 1.1×$10^4$-1.8×$10^6$). There were 262 miRNAs present (raw counts >0) in all 50 samples. There were no miRNAs universally present in one sample group (pre- or post-exercise) and universally absent in another. The closest any miRNA came to this expression pattern was pre-miR-206, which was present in 15 saliva samples pre-run, but only 6 samples post-run. Notably, alterations in miR-206 have been observed in previous miRNA exercise studies. Among the remaining 26 "exercise" miRNAs interrogated, 11 were absent in all 50 samples. This was also true for 7/25 (28%) of "concussion" miRNAs.

Figure 2:
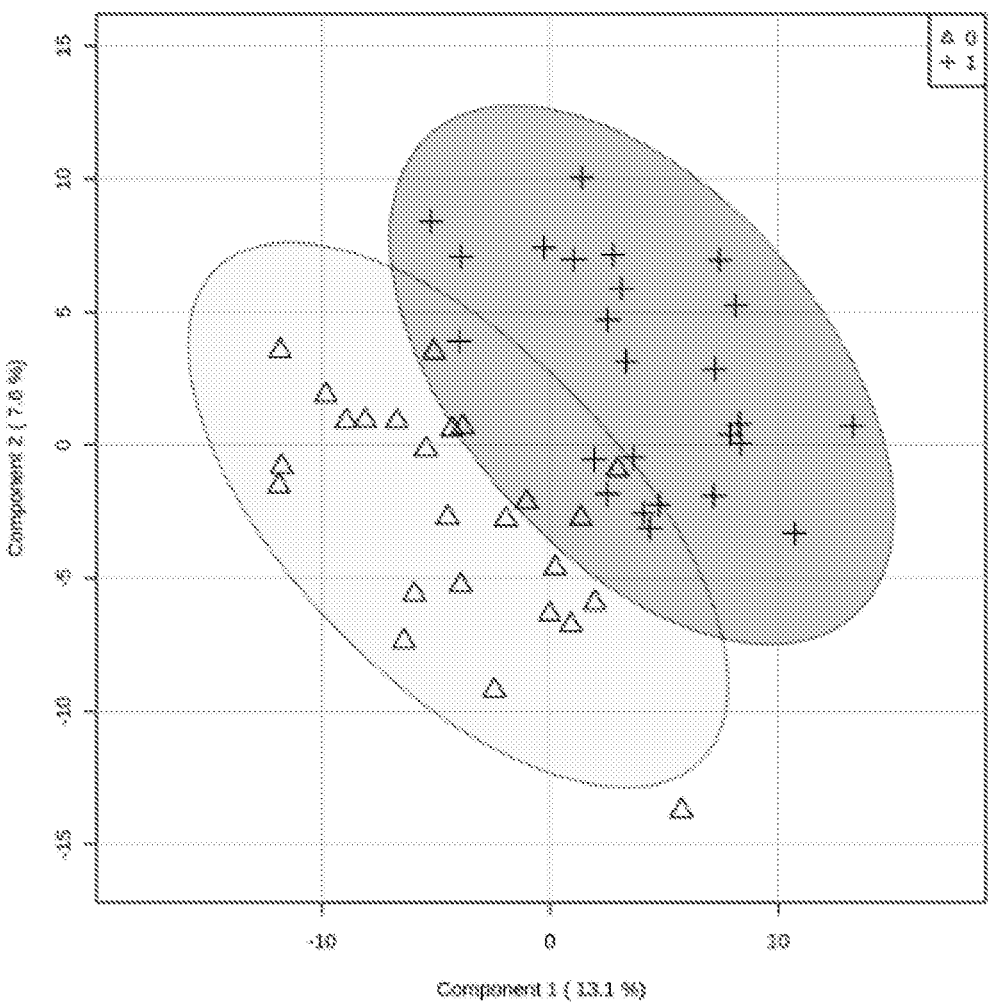
FIG. 2. Total salivary miRNA expression differentiates pre- and post-run samples A two-dimensional partial least squares discriminant analysis using the expression profile of 460 salivary miRNAs (precursor and mature) resulted in nearly complete separation of pre-run (+, 1) and post-run (Δ, 0) samples (n=25), while accounting for 20.7% of the variance in expression. The 95% confidence interval for sample dispersion is noted by the shaded ovals.
Figure 4A:
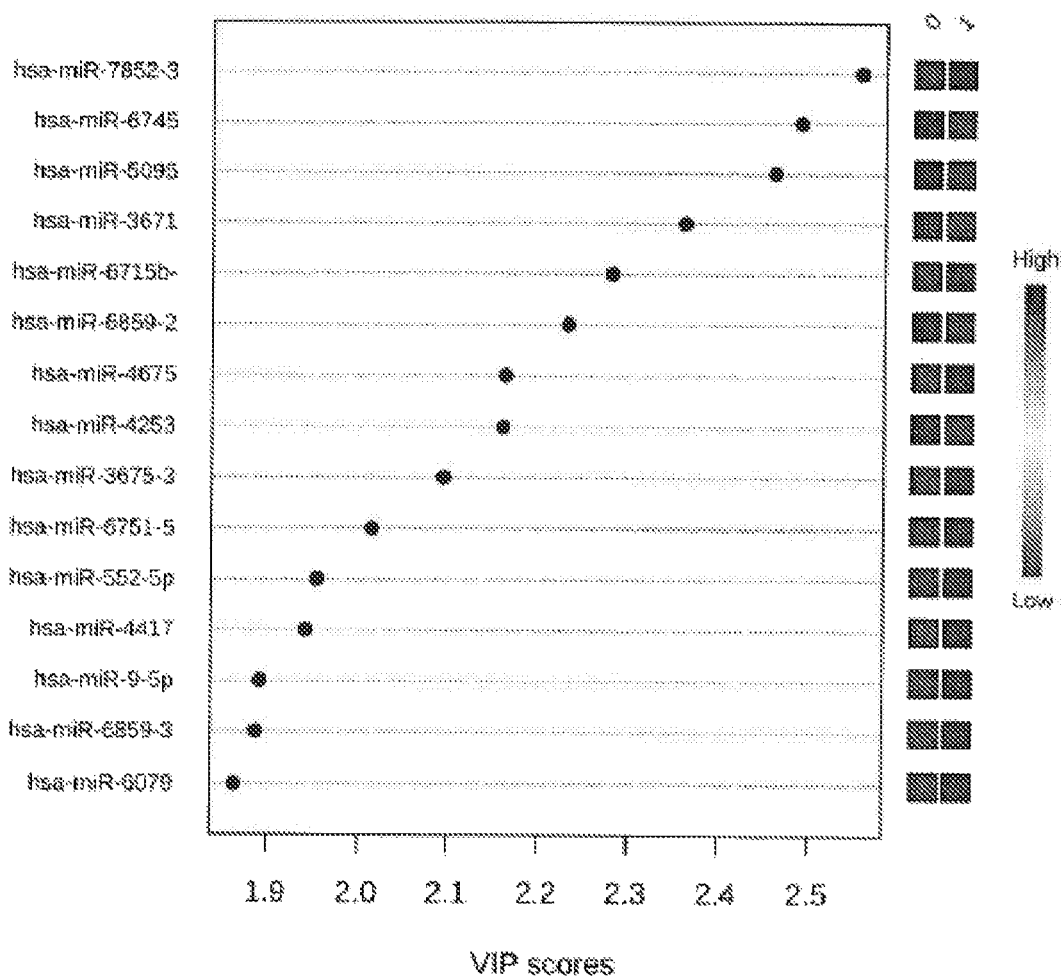
FIG. 4A (Supplemental FIG. 1). Expression levels of 15 salivary miRNAs segregate pre- and post-run samples Expression levels for the 15 salivary miRNAs with the largest variable importance in projection scores on partial least squares discriminant analysis were used to perform hierarchical clustering of individual samples with a Pearson distance metric and a complete clustering algorithm. This approach segregated all but 5/25 of the pre-run samples (0, red), and 3/25 (12%) of the post-run samples (1, green). Note that "mis-clustered" samples tended to co-localize with associated pre- or post-run saliva from the same individual, belying the contributions of individual variation to salivary miRNA profiles. The individual miRNA pairs most closely clustered were miR-6859-2-5p/miR-4253, and miR-552-5p/miR-4417.
Figure 4B:
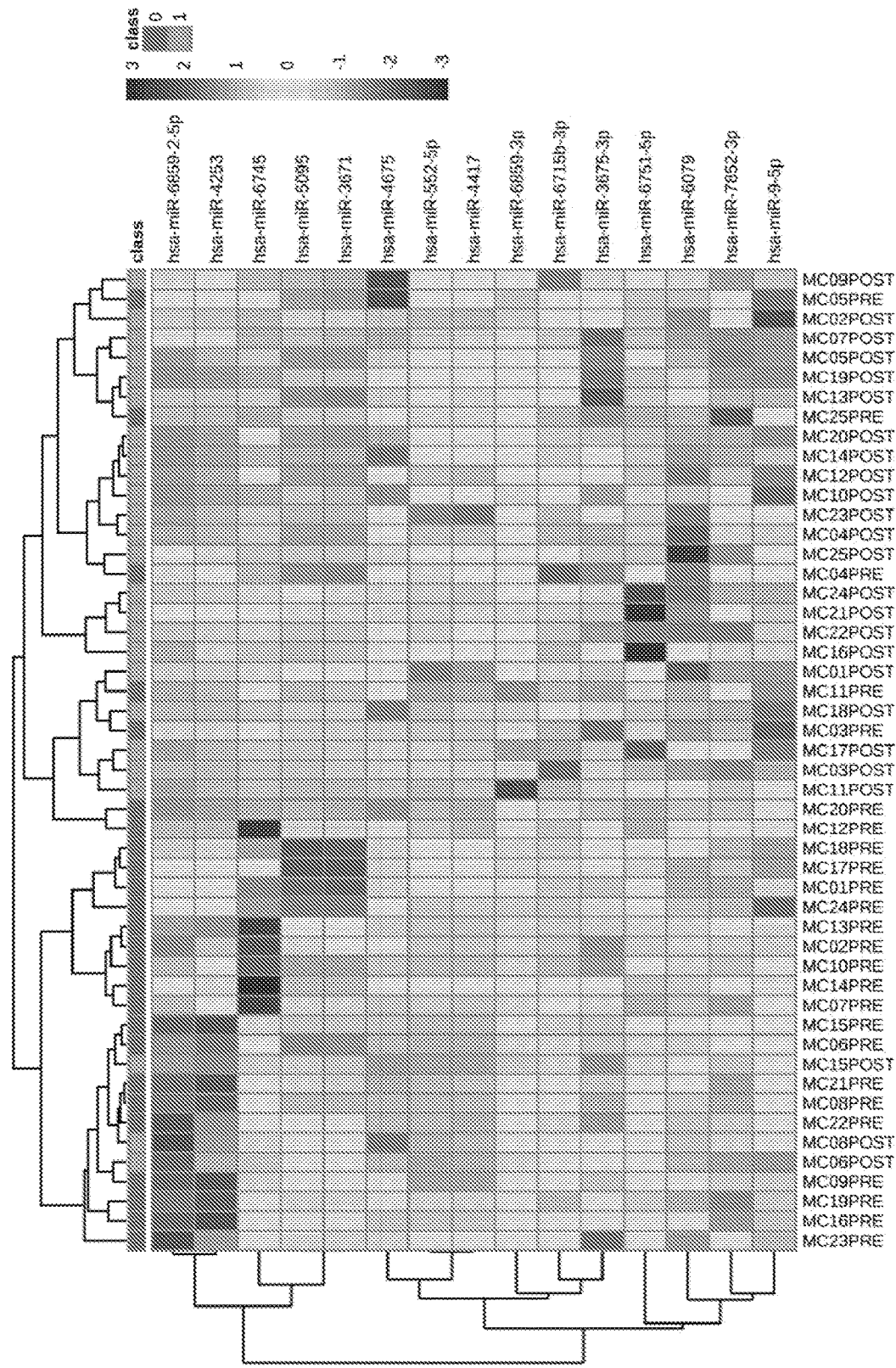
FIG. 4B. Visualization of salivary miRNA pre- and post-run changes across individual samples.

Running-induced miRNA changes. There were 122 salivary miRNAs with significant (FDR<0.05) changes post-run (Supplemental Table 2). Sixty-three miRNAs were down-regulated post-run and 59 were up-regulated. There was one miRNA down-regulated in all 25 post-run samples (miR-7154-3p, V-stat<0.0001, FDR=2.63E-5). One of the 122 miRNAs had been identified in previous exercise studies (pre-miR-206, FDR=0.035, V-stat=146), and two miRNAs were identified in "concussion" studies (miR-200b-3p, V-stat=242, FDR=0.035; miR-30e-5p, V-stat=26, FDR=0.0036). There were 8 miRNAs with significant (FDR<0.05) and highly consistent changes (>23/25 samples) post-run (FIG. 1). Six of these miRNAs were elevated post-run (miR-7154-3p, miR-200b-5p, miR-5582-3p, miR-6859-3p, miR-6751-5p, and miR-4419a), and two were decreased (miR-3671, miR-5095). A two-dimensional PLSDA using total salivary miRNA profiles for each participant resulted in nearly complete separation of pre- and post-run samples, while accounting for 20.7% of the variance in expression (FIG. 2). Hierarchical clustering using the 15 miRNAs segregated all but 5/25 (20%) of the pre-run samples, and 3/25 (12%) of the post-run samples (FIG. 4/Supplementary FIG. 1). Notably, 5/8 "mis-clustered" samples cluster with their pre- or post-run counterpart. The fifteen miRNAs were largely clustered into ten that were up-regulated post-run and five that were down-regulated. The strongest miRNA clustering was observed for miR-6859-2-5p/miR-4253, and miR-552-5p/miR-4417.

Predicted microRNA targets. To explore the function of salivary miRNA changes, the eight miRNAs most significantly altered post-run were interrogated for predicted gene targets. These eight miRNAs targeted 2,389 mRNAs (microT-cds>0.90, p<0.05). The largest number of mRNAs (1,159) was targeted by miR-5582-3p (Supplementary Table 3A). The 2,389 mRNA targets over-represented (FDR<0.05) 15 KEGG pathways (Supplementary Table 4A), including pathways related to metabolism (glycerophospholipid metabolism, p=0.042; 17 genes, 6/8 miRNAs), water balance (aldosterone-regulated sodium reabsorption, p=0.049, 12 genes, 5/8 miRNAs), and cardiac conduction (arrhythmogenic right ventricular cardiomyopathy, p=0.018, 12 genes, 4/8 miRNAs). Interestingly, four distinct brain-related pathways that were also over-represented (Wnt signaling, p=4.0E-5, Morphine addiction, p=0.0033; GABAergic synapse, p=0.00016; Prolactin signaling, p=0.0035).

Overlapping changes in mRNA/microRNA expression. The 122 miRNAs "altered" post-run (FDR<0.05) targeted 140 mRNA transcripts that were detectable and nominally altered (FDR<0.1) in post-run saliva (Supplemental Table 5). This represented 53% (140/269) of the total saliva mRNA changes detected post-run, and exceeded the number of miRNA-mRNA interactions expected by chance alone (p<0.0001). Among the 122 miRNAs of interest, 96 (79%) targeted at least one transcript altered in post-run saliva. The miRNA that targeted the largest number of genes with post-run salivary changes was miR-4419a (25 mRNA targets). Fifty-four of the 122 miRNAs targeted five or more "altered" transcripts. The transcript targeted by the largest number of "altered" miRNAs was SESN3 (11 miRNAs). Fifty-nine of the 269 transcripts were targeted by three or more miRNAs of interest. These 59 mRNAs demonstrated a significant number of protein-protein interactions (p=0.021) in String analysis, with 12 edges, and a clustering coefficient of 0.167. The protein domains significantly enriched among these miRNA targets were myosin tail (FDR=0.024), and myosin N-terminal SH3-like (FDR=0.024). Among the altered mRNAs and miRNAs with predicted target interactions, 26 demonstrated correlations (R>[0.40]) in concentration change post-run (Table 2). Six of the miRNA/mRNA post-run changes were inversely correlated and the remainder was positively correlated. The largest number of miRNA/mRNA target correlations were observed for CSF2RB (n=4) and MYSM1 (n=4). The strongest correlation was observed between TAL1 and miR-605-3p (R=0.71).

TABLE 2

Associations between microRNA changes and target mRNA changes in saliva

| mRNA | microRNA | Post-run Δ (mRNA/ miRNA) | Pearson R (p-value) | Target Prediction Strength |
|---|---|---|---|---|
| ARID1A | miR-9-5p | ↑/↓ | -0.43 (0.001) | 94 |
| CSF2RB | miR-5698 | ↑/↓ | -0.49 (0.0003) | 80 |
|  | miR-181a-5p | ↑/↓ | -0.42 (0.002) | 68 |
|  | miR-1273f | ↑/↑ | 0.48 (0.0004) | 69 |
|  | miR-4419a | ↑/↑ | 0.51 (0.0001) | 71 |
| BRMS1L | miR-3671 | ↓/↓ | 0.52 (7.2E-7) | 52 |
| G3BP2 | miR-4253 | ↓/↓ | 0.41 (0.002) | 71 |
| FJX1 | miR-4419a | ↑/↑ | 0.44 (0.0009) | 53 |
| JAK3 | miR-6751 | ↑/↑ | 0.41 (0.002) | 95 |
| KAT2B | miR-181b-5p | ↑/↑ | 0.42 (0.001) | 50 |
|  | miR-7852-3p | ↑/↑ | 0.44 (0.001) | 59 |
| HOXB9 | miR-4251 | ↓/↓ | 0.40 (0.003) | 52 |
| MAP4K5 | miR-429 | ↓/↓ | 0.49 (0.0002) | 99 |
| MYSM1 | miR-548ac | ↓/↑ | -0.45 (0.001) | 69 |
|  | miR-6737-3p | ↓/↑ | -0.43 (0.001) | 72 |
|  | miR-429 | ↓/↓ | 0.46 (0.0006) | 52 |
|  | miR-936 | ↓/↓ | 0.45 (0.001) | 65 |
| PREX1 | miR-1915-3p | ↑/↑ | 0.47 (0.0005) | 72 |
| PIAS2 | miR-200a-3p | ↑/↑ | 0.51 (3.1E-6) | 77 |
|  | miR-4418 | ↑/↑ | 0.59 (6.1E-8) | 58 |
| OLIG1 | miR-4488 | ↑/↑ | 0.46 (0.0007) | 76 |
| SOX8 | miR-6124 | ↑/↑ | 0.40 (0.003) | 75 |
| SORL1 | miR-3671 | ↑/↓ | -0.45 (0.0009) | 92 |
| TAL1 | miR-605-3p | ↓/↓ | 0.71 (1.0E-8) | 61 |
| ZNF536 | miR-4419a | ↑/↑ | 0.42 (0.002) | 73 |
| ZBTB5 | miR-302e | ↑/↑ | 0.42 (0.002) | 97 |

Direction of change for each mRNA/microRNA pair are denoted by arrows. For all mRNAs reported, the level of significance for post-run changes is FDR ≤ 0.1. For All reported microRNAs, the level of significance for post-run changes is FDR ≤ 0.05. Strength of evidence for predicted mRNA/microRNA interaction is denoted by micro-T-cds score, where 100 indicates the strongest possible, experimentally-validated interaction.

Correlations between post-run miRNA changes and participant characteristics.

Demographic and exercise characteristics of interest were also evaluated for associations with post-run changes in salivary miRNA expression using Pearson (continuous variables) or Spearman Rank (dichotomous variables) testing (Supplementary Table 6). No miRNA changes were associated (R>[0.5], FDR<0.15) with time of sample collection post-run. Eight miRNAs were associated with run duration (minutes), but none of the miRNAs were associated with run distance (km) or pace of the run (minutes/km). There were no associations between post-run miRNA changes and post-run changes in temperature, systolic blood pressure, or diastolic blood pressure. However, there were 24 miRNA levels associated with post-run heart rate changes (bpm). There were two miRNA changes associated with time since last meal, but no miRNAs associated with presence/absence of dietary restrictions. There were 23 miRNAs with post-run changes associated with female sex. Two miRNA changes were associated with participant age. Of the 8 miRNAs with the most robust post-run changes on Wilcoxon testing, two had associations with female sex: miR-5095, and miR-6859-3p. None of the other variables showed significant associations with these 8 miRNAs.

The influence of sex on miRNA responses to exercise. A two way ANOVA was employed to further examine the relationship between female sex and the salivary miRNA response to exercise. There were 13 miRNAs that differed (FDR<0.05) between male and female subjects and two of these miRNAs displayed robust interaction with post-run exercise status (FIG. 3). Both miR-6745 (FDR=0.00025) and miR-6746-3p (FDR=0.032) were decreased post-run in female subjects, but not in male subjects. A third miRNA, miR-4675, demonstrated differences among male/female subjects (FDR=0.034) and pre-/post-run status (FDR=0.037), but no interaction between sex and post-run status (FDR=0.94).

Figure 5:
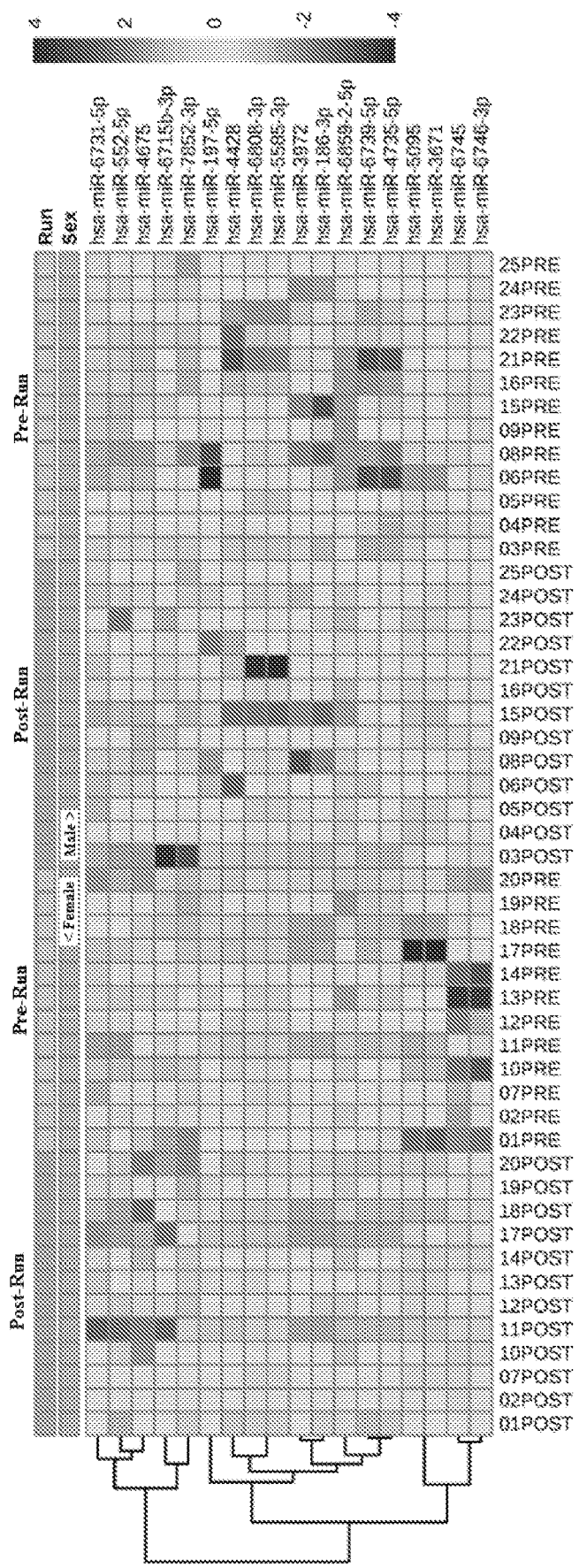
FIG. 5 (Supplemental FIG. 2). Visualization of sex-specific salivary miRNA changes across individual samples. A hierarchical clustering approach utilized individual expression levels for the 18 miRNAs influenced by run-status or sex on two-way analysis of variance (FDR<0.05) to visualize patterns of salivary miRNA expression in female (purple; n=12) and male (green; n=13) participants pre-run (blue) and post-run (pink). Five miRNAs tended to increase post-run only in female subjects. Four miRNAs tended to decrease post-run only in female subjects. Nine miRNAs demonstrated relatively consistent expression in male participants but displayed low patterns of expression in female runners both before and after the run.
Figure 6:
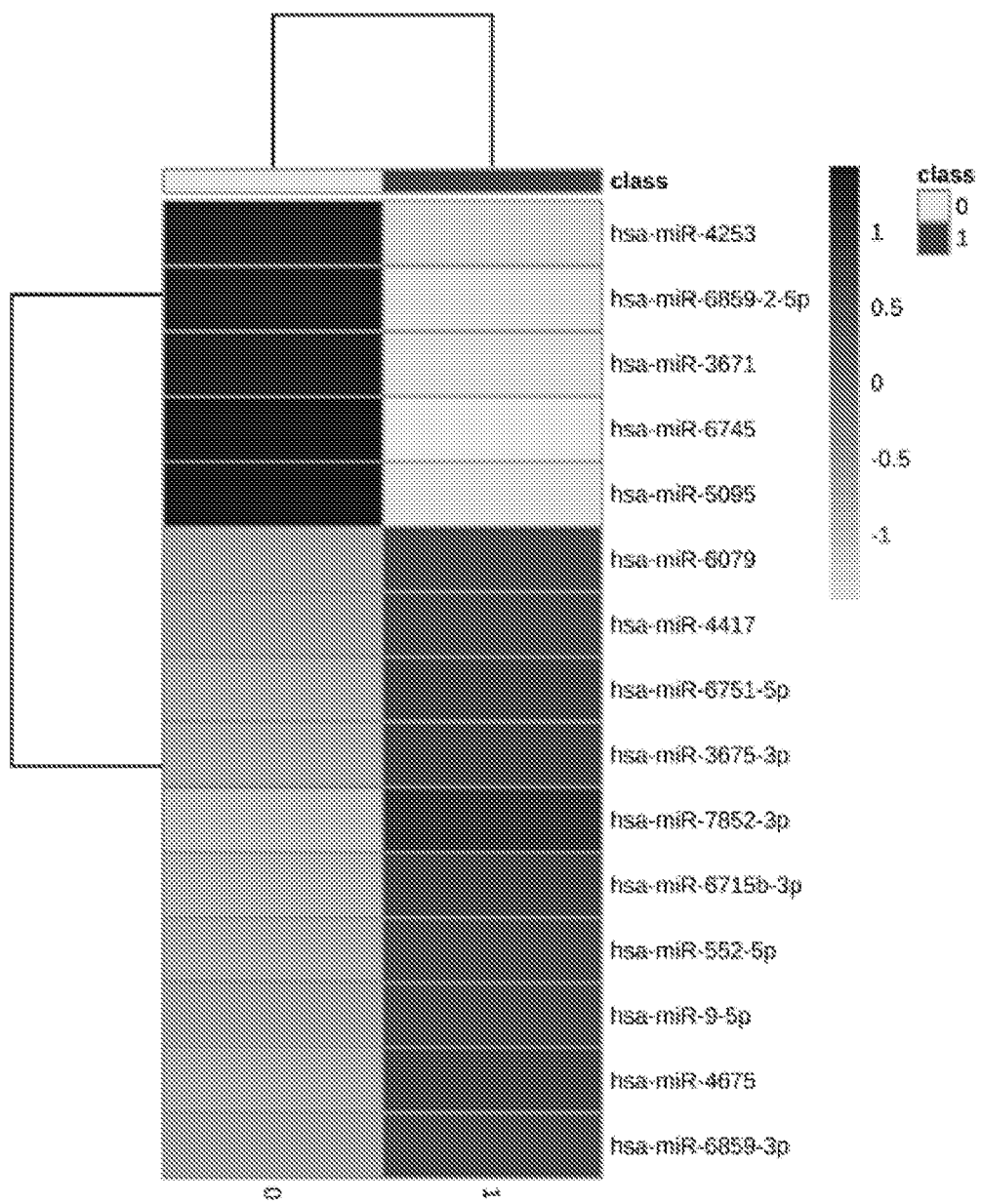
FIG. 6 (Supplementary FIG. 1-1). Hierarchical clustering using the 15 miRNAs most critical for sample projection on PLSDA segregated all but 5/25 (20%) of the pre-run samples, and 3/25 (12%) of the post-run samples. The fifteen miRNAs were largely clustered into ten that were up-regulated post-run and five that were down-regulated.

Hierarchical clustering was used to visualize patterns of salivary miRNA expression among male and female subjects before and after running by using the 18 miRNAs with the most robust interactions between sex and post-run status (FIG. 5/Supplementary FIG. 2).

Three clusters of miRNA trends emerged: 1) There were 5 miRNAs that tended to increase post-run only in female subjects; 2) There were four miRNAs that tended to decrease post-run only in female subjects; and 3) There were nine miRNAs with relatively consistent expression in male participants that demonstrated low patterns of expression in female runners both before and after the run. The three salivary miRNAs with unique post-run alterations in female participants targeted 265 miRNAs (Supplementary Table 3B) that over-represented four KEGG pathways (Supplementary Table 4B). Three of the four over-represented pathways involved biosynthesis (Fatty acid biosynthesis, p=4.9E-32, 3 genes, 1/3 miRNAs; Glycosphingolipid biosynthesis, p=0.0021, 2 genes, 2/3 miRNAs), or metabolism processes (Fatty acid metabolism, p=1.7E-8, 3 genes, 1/3 miRNAs).

Utilizing high throughput sequencing techniques, the inventors identified a number of novel miRNAs that are altered in saliva following endurance exercise. The downstream genetic pathways targeted by these miRNAs involve metabolic processes (glycerophospholipid metabolism) and fluid regulation (aldosterone-regulated sodium reabsorption). In addition, circulating salivary miRNAs demonstrated enrichment for systemic targets, such as cardiac conduction (arrhythmogenic right ventricular cardiomyopathy), a finding underscored by the large number of miRNAs associated with post-run changes in heart rate (Supplementary Table 6).

These data show that salivary miRNA measurement may provide a non-invasive "liquid biopsy" of the systemic epi-transcriptome response in humans. Further support for this idea can be found through interrogation of the individual genes targeted by miRNAs post-run. For example, 11 of the 122 (9%) miRNAs that changed after endurance running targeted expression of SESN3, a transcript that was increased in saliva post-run (Supplemental Table 5). The SESN3 gene encodes a sestrin family protein that is induced by stress and reduces levels of intracellular reactive oxygen species; Hagenbuchner, J., Kuznetsov, A., Hermann, M., Hausott, B., Obexer, P., &. Ausserlechner, M. J. (2012). FOXO3-induced reactive oxygen species are regulated by BCL2L11 (Bim) and SESN3. *J Cell Sci,* 125(5), 1191-1203. Interestingly, the SESN3 protein product is critical for normal regulation of blood glucose, and is dysregulated in insulin resistance and obesity; Lee, J. H., Budanov, A. V., Talukdar, S., Park, E. J., Park, H. L., Park, H. W., . . . & Wolfe, A. M. (2012). Maintenance of metabolic homeostasis by Sestrin2 and Sestrin3. *Cell metabolism,* 16(3), 311-321. Thus, down-regulation of the miRNAs that target SESN3 may permit up-regulation of this adaptive response during endurance exercise.

Remarkably, of the 269 mRNAs with post-run salivary changes, 59 (22%) were targeted by three or more miRNAs with post-run changes. Analysis of these 59 mRNAs revealed a significant number of putative interactions between their protein products, suggesting targeted regulation of a transcriptional network. In fact, the KEGG pathways with the most significant enrichment among this group were myosin-related proteins, which may play a role in musculoskeletal adaptations to endurance exercise. Another miRNA-mRNA interaction between miR-605-3p and its gene target, TAL1 appeared uniquely geared towards endurance running adaptation. Levels of miR-605-3p and TAL1 were robustly down-regulated after exercise in a highly correlated manner (Table 2).

The TAL1 protein product is implicated in erythroid differentiation and stimulated by erythropoietin, but may be reduced through miR-605-3p-mediated cleavage; Prasad, K. S., Jordan, J. E., Koury, M. J., Bondurant, M. C., & Brandt, S. J. (1995). Erythropoietin stimulates transcription of the TAL1/SCL gene and phosphorylation of its protein products. *Journal of Biological Chemistry,* 270(19), 11603-11611. The paradoxical direct correlation between TAL1 and miR-605-3p could be explained by a phase shift in expression, wherein down-regulation of miR-605-3p permits the translation and exhaustion of TAL1 mRNA reserves.

Surprisingly, the eight miRNAs with the most robust post-run changes also targeted a number of brain-related transcripts involved in processes such as Wnt Signaling, GABAergic synapse, and morphine addiction (Supplementary Table 4A). This finding is consistent with previous reports that salivary miRNA may provide a window into central nervous system function; Hicks, S. D., Johnson, J., Carney, M. C., Bramley, H., Olympia, R. P., Loeffert, A. C., & Thomas, N. J. (2018), Overlapping microRNA expression in saliva and cerebrospinal fluid accurately identities pediatric traumatic brain injury. *Journal of neurotrauma,* 35(1), 64-72; Hicks, S. D., Ignacio, C., Gentile, K., & Middleton, F. A. (2016). Salivary miRNA profiles identify children with autism spectrum disorder, correlate with adaptive behavior, and implicate ASD candidate genes involved in neurodevelopment. *BMC pediatrics,* 16(1), 52.

Indeed, several of the mRNA/miRNA pairs with associated post-run changes are implicated in neuronal-related processes (Table 2). For instance, ARID1A is up-regulated post-run, and forms an integral part of the neural-progenitors-specific chromatin remodeling complex (npBAF) that is required for proliferative control in neural stem cells; Lessard, J,, Wu, J. I., Ranish, J. A., Wan, M., Winslow, M. M., Staahl, B. T., . . . & Crabtree, G. R. (2007). An essential switch in subunit composition of a chromatin remodeling complex during neural development. *neuron,* 55(2), 201-215. Decreased levels of miR-9-5p (which regulates npBAF and display inverse associations with ARID1A post-run) may facilitate the contributions of endurance exercise to hippocampal neurogenesis, potentiation, and memory; Yoo, A. S., Staahl, B. T., Chen, L., & Crabtree, G. R. (2009). MicroRNA-mediated switching of chromatin-remodelling complexes in neural development. *Nature,* 460(7255), 642 Van Praag, H., Christie, B. R., Sejnowski, T, J., & Gage, F. EL (1999). Running enhances neurogenesis, learning, and long-term potentiation in mice. *Proceedings of the National Academy of Sciences,* 96(23), 13427-13431.

It is notable that four of the eight miRNAs most robustly changed in post-run saliva target 18 mRNAs implicated in morphine addiction (Supplemental Table 4A). In the context of endurance exercise, these miRNAs may promote an endorphin response that underlies the experience of a "runner's high" (euphoria associated with prolonged running). This possibility is supported by the observation that eight miRNAs demonstrate significant correlations (R>[0.40]) with run duration (Supplemental Table 6), a critical component for runner's high ascertainment. In addition, five of the eight miRNAs associated with run duration also target nine morphine-related genes, a greater enrichment than expected by chance alone (FDR=9.7E-7). Given these intriguing connections, further exploration of this potential mechanism is certainly warranted.

A novel finding of the current study is the unique influence of participant sex on the peripheral miRNA response to exercise. Previous studies have demonstrated that females have distinct cardiovascular, metabolic, and musculoskeletal responses to exercise training; Blumenthal, J. A., Emery, C. F., Madden, D. J., George, L. K., Coleman, R. E., Riddle, M. W., . . . & Williams, R. S. (1989). Cardiovascular and behavioral effects of aerobic exercise training in healthy older men and women. *Journal of gerontology,* 44(5), M147-M157; Tarnopolsky, M. A. (2000). Gender differences in substrate metabolism during endurance exercise. *Canadian Journal of Applied Physiology,* 25(4), 312-327; Magkos, F. Kavouras, S. A., Yannakoulia, M., Karipidou, M. Sidossi, S., & Sidossis, L. S. (2007). The bone response to non-weight-bearing exercise is sport site-, and sex-specific.

*Clinical Journal of Sport Medicine,* 17(2), 123-28. In skeletal muscle, these differences may be attributed, in part, to disparate transcriptional responses to resistance exercise; Morton, J. P., Kayani, A. C., McArdle, A., & Drust, B. (2009). The exercise-induced stress response of skeletal muscle, with specific emphasis on humans. *Sports medicine,* 39(8), 643-662. Here, the inventors show that post-run changes in the levels of 23 salivary miRNAs are associated with female sex, and 3 miRNAs display potential sex-exercise interactions on two-way ANOVA (FIG. 3). Together, gene targets for these three miRNAs over-represent metabolic targets (Supplemental Table 4b). In particular, miR-6745 targets three mRNAs (FASN, ACACB, and ACSL4) implicated in fatty acid biosynthesis. Among these targets, FASN has been implicated in the acute exercise response of skeletal and hepatic tissue; Fu, Liu, X Niu, Y., Yuan, H., Zhang, N., & Lavi, E. (2012). Effects of high-fat diet and regular aerobic exercise on global gene expression in skeletal muscle of C57BL/6 mice. *Metabolism-Clinical and Experimental,* 61(2), 146-152; Hoene, M Lehmann, R., Hennige, A. M., Pohl, A. K., Häring, H. U., Schleicher, E. D., & Weigert, C. (2009). Acute regulation of metabolic genes and insulin receptor substrates in the liver of mice by one single bout of treadmill exercise. *The Journal of physiology,* 587(1), 241-252. Interactions between miR-6745 and FASN may be partially responsible for the unique fatty acid kinetics observed in females during exercise and weight-loss regimens; Talanian, J. L., Galloway, S. D., Heigenhauser, G. J., Bonen, A., & Spriet, L. L. (2007). Two wheels of high-intensity aerobic interval training increases the capacity for fat oxidation during exercise in women. *Journal of applied physiology,* 102(4), 1439-1447; Mittendorrer, B. Magkos., F. Fabbrini., E. Mohammed., B. S., & Klein, S. (2009), Relationship between body fat mass and free fatty acid kinetics in men and women. *Obesity,* 17(10), 1872-1877.

Of the 27 miRNAs interrogated in previous exercise studies, 12 were reliably detected in pre- and post-run saliva. Only one of these, pre-miR-206, was altered post-run, demonstrating significant down-regulation. This deviates from a study of blood miRNAs in 14 male athletes post-marathon that demonstrated up-regulation of miR-206 immediately post-run. It is possible that systemic increases in miR-206 following endurance exercise may be facilitated by processing and exhaustion of precursor miR-206 stores observed here. Previous exercise studies include those described by Baggish, Aaron L., et al. "Dynamic regulation of circulating microRNA during acute exhaustive exercise and sustained aerobic exercise training." The Journal of physiology 589.16 (2011): 3983-3994; Uhlemann, Madlen, et al. "Circulating microRNA-126 increases after different forms of endurance exercise in healthy adults." European journal of preventive cardiology 21.4 (2014): 484-491; Mooren, Frank C., et al. "Circulating microRNAs as potential biomarkers of aerobic exercise capacity." American Journal of Physiology-Heart and Circulatory Physiology 306.4 (2014): H557-H563; Banzet, Sébastien, et al. "Changes in circulating microRNAs levels with exercise modality." Journal of applied physiology 115.9 (2013): 1237-1244. Aoi, Wataru, et al. "Muscle-enriched microRNA miR-486 decreases in circulation in response to exercise in young men." Frontiers in physiology 4 (2013).

Alternatively, miR-206 may target alternative transcripts in blood and saliva, thus undergoing paradoxical shifts in the two biofluid spaces. The majority of previously described "exercise-related" miRNAs were studied based on their specificity to cardiac or skeletal muscle tissue. Thus, it is not completely surprising that many of these miRNAs are not robustly expressed in saliva. The one previous study of salivary miRNAs in 19 men undergoing cycling exercise identified changes in miR-33a and miR-378a. The present study found no changes in miR-33a and did not detect miR-378a in the saliva of the 25 participants. However, salivary levels of miR-378f, which shares an identical seed sequence (UCCUGAC) with miR-378a, were up-regulated post-run in 17/25 participants (FDR=0.03; Supplementary Table 2).

Like the previous salivary miRNA exercise study, the inventors found that the miRNAs altered post-run were enriched for lipid metabolism targets. Differences in the individual miRNAs identified between these two studies may be explained by the female composition of our cohort, the use of an RNA-sequencing approach, or differences induced by running versus cycling exercise. The later variable may be particularly important given the finding by Banzet and colleagues, id. (2013) that changes in circulating miRNA levels are dependent on exercise modality (concentric versus eccentric exercise).

Another important finding of this study was that the majority of salivary miRNAs previously identified as potential biomarkers of concussion are not changed post run. Of the 25 salivary miRNAs identified in previous concussion studies of Hicks, S. D., Johnson, J., Carney, M. C., Bramley, H., Olympia, R. P., Loeffert, A. C., & Thomas, N. J. (2018). Overlapping microRNA expression in saliva and cerebrospinal fluid accurately identifies pediatric traumatic brain injury. *Journal of neurotrauma,* 35(1), 64-72; and Johnson, J. J., Loeffert, A. C., Stokes, J., Olympia, R. P., Bramley, H., Hicks, S. D. (2018). Association of salivary microRNA changes with prolonged concussion symptoms. *JAMA pediatrics,* only two (miR-200b-3p and miR-30e-5p) were altered post-run. This finding highlights the suitability of salivary miRNA as a biomarker for exercise-related concussion.

Given their running-induced changes, miR-200b and miR-30e-5p may not be ideal for field-side concussion identification. However, these two miRNAs may still be suitable as therapeutic biomarkers that can be tracked longitudinally in the weeks following concussion (especially since miR-30e predicts prolonged concussion symptoms).

In light of findings that post-concussion exercise regimens may speed symptom recovery, it is notable that levels of exercise-induced changes in these two miRNAs oppose the direction of change observed in post-concussion saliva; Baker, J. G., Freitas, M. S., Leddy, J. J., Kozlowski, K. F., & Willer, B. S. (2012). Return to full functioning after graded exercise assessment and progressive exercise treatment of post-concussion syndrome. *Rehabilitation research and practice,* 2012.

Leddy, J. J., Kozlowski, K., Donnelly, J. P., Pendergast, D. R., Epstein, & Willer, B. (2010). A preliminary study of subsymptom threshold exercise training for refractory post-concussion syndrome. *Clinical Journal of Sport Medicine,* 20(1), 21-27. For example, miR-30e is lower in children with prolonged concussion symptoms (compared to those with acute symptom resolution), but is increased by endurance running; Johnson, J. J., Loeffert, A. C., Stokes, J., Olympia, R. P., Bramley, H., & Hicks, S. D. (2018). Association of salivary microRNA changes with prolonged concussion symptoms. *JAMA pediatrics.* MiR-200b is increased in the saliva of children with prolonged concussion symptoms, but is decreased by endurance running. Together, miR-30e and miR-200b target 1261 mRNAs involved in axon guidance (p=7.08E-6, 24 genes), morphine addiction (p=0.012, 8 genes), long-term depression (p=0.012, 6 genes), and neurotrophin signaling (p=0.036, 18 genes). Future studies tracking these miRNAs in concussed patients who are undergoing treatment may provide an objective window into brain recovery.

The inventors consider this the largest study of miRNA expression in human athletes (n=25) and the first to examine the entire micro-transcriptome (all 4,694 known miRNAs) in exercising human participants. The current comparison of male and female miRNA responses to endurance running provides novel insight into the sex-specific physiologic mechanisms that may occur at the transcript level. Nonetheless, there are several limitations to the current study to be noted. Certainly, analysis of miRNA from muscle or blood samples with the current high throughput approach would offer additional information about the aggregate human response to exercise.

Unfortunately, such samples were not available for the current study. Future investigations interrogating global miRNA levels alongside physiologic markers (e.g. creatinine kinase, aspartate aminotransferase) and measures of exercise capacity (e.g. maximum oxygen uptake, anaerobic lactate threshold) would also provide valuable contextual data for interpretation. It should be noted that the current design employed a non-controlled exercise regimen in which participants completed a range of running courses with slight variations in intensity (rather than using a common treadmill-based regimen). Such an approach makes replicability difficult, but does provide a realistic setting, in which competitive distance runners typically train.

By examining associations between course mileage and run speed the inventors attempted to control for some of the variation between individual running experiences. Although the current study is among the first to begin exploring downstream changes in gene targets of exercise-related miRNAs, the filtering parameters (RNAs≤50 base pairs) employed in library generation and sequence alignment may have limited recognition of mRNA targets. This approach eliminates many mRNA candidates with sequences>50 base pairs that may be influenced by exercise. Thus, the absence of mRNAs of interest from Table 2 may represent type II errors, and should not be assumed to represent a lack of mRNA-exercise response.

As shown above, a compelling number of salivary miRNAs demonstrate changes in concentration following sustained aerobic exercise. The salivary miRNAs with the largest changes target physiologically relevant pathways, including metabolism, fluid regulation, and cardiac conduction. This miRNA response is influenced in a sex-specific manner, particularly for a subset of miRNAs involved in fatty acid biosynthesis. Thus, salivary miRNAs may provide insight into a number of adaptive responses to aerobic training, and represent an easily accessible biomarker in endurance athletes.

Other Observations and Findings 8 miRNA changes were associated with the length of a run. While not being bound to any particular explanation, it is possible that these miRNAs modulate conversion to ketone metabolism in a long run. The degree of these changes may be used to evaluate or monitor metabolism of a subject and to select a health or training regimen. Optimizing training and performance through regimen and nutrition strategies is central to supporting elite sportspeople, much of which has focused on manipulating the relative intake of carbohydrate and fat and their contributions as fuels for energy provision. The ketone bodies, namely acetoacetate, acetone and β-hydroxybutyrate (βHB), are produced in the liver during conditions of reduced carbohydrate availability and serve as an alternative fuel source for peripheral tissues including brain, heart and skeletal muscle. Ketone bodies are oxidised as a fuel source during exercise, are markedly elevated during the post-exercise recovery period, and the ability to utilize ketone bodies is higher in exercise-trained skeletal muscle. The metabolic actions of ketone bodies can alter fuel selection through attenuating glucose utilization in peripheral tissues, anti-lipolytic effects on adipose tissue, and attenuation of proteolysis in skeletal muscle. Moreover, ketone bodies can act as signaling metabolites, with βHB acting as an inhibitor of histone deacetylases, an important regulator of the adaptive response to exercise in skeletal muscle. Recent development of ketone esters facilitates acute ingestion of βHB that results in nutritional ketosis without necessitating restrictive dietary practices. Initial reports suggest this strategy alters the metabolic response to exercise and improves exercise performance, while other lines of evidence suggest roles in recovery from exercise; see Evans, M., Cogan, K. E. and Egan, B. (2017), Metabolism of ketone bodies during exercise and training: physiological basis for exogenous supplementation. J Physiol, 595: 2857-2871. doi:10.1113/JP273185 (incorporated by reference).

24 miRNAs changes were associated with heart rate changes post-run. While not being bound to any particular explanation, it is possible that these miRNAs modulate remodeling of the cardiovascular system that occurs with endurance exercise. The degree of these changes may be used to evaluate or monitor cardiovascular activity in a subject and to select a health or training regimen. Conventionally, target and maximum heart rates for individuals of a particular age group are used to select an health or exercise regimen, seehttps://healthyforgood.heart.org/move-more/articles/target-heart-rates (last accessed Jan. 25, 2018, incorporated by reference). The inventors have provided an alternative or complementary way to monitor cardiovascular activity by simple measurement of miRNAs associated with optimal cardiovascular exercise and performance. Monitoring of such miRNAs may also be used to select a weight-loss reginmen.

23 miRNA changes were associated with female sex. While not being bound to any particular explanation, it is possible that females have different physiologic responses than males to endurance running, such as differences in metabolism, bone remodeling, cardiovascular remodeling, or stress relief. The presence or degree of these changes may be used to evaluate or monitor metabolism to distinguish female and male subjects or to tailor or individualize a health or training regimen suitable for a female (or male) subject.

Most of the miRNAs used as concussion biomarkers are not changed post-run. These miRNAs which are altered post-run, but not associated with sports concussion may be excluded from analysis of miRNA levels associated with concussion. However, two miRNAs associated with concussion—mirR-30e and miR-200b were altered post-run.

While these two miRNA biomarkers may not be ideal candidates for distinguishing exercising subjects from exercising subjects having TBI or concussions, they may be useful for distinguishing between subjects exercising at different intensities or used to distinguish between acute concussion syndrome ("ACS") and prolonged concussion syndrome ("PCS"). The level of miR-30e is also increased in saliva and CSF for subjects with TBI compared to controls and is higher in children with ACS (acute concussion syndrome) compared to those with PCS (prolonged concussion syndrome). In contrast, the level of miR-200b is increased in PCS compared to ACS.

Non-limiting embodiments of the invention include the following:

1. A method for detecting or diagnosing a risk of concussion, mTBI or TBI in a subject comprising:
   detecting in saliva of a subject a level of one or more microRNAs ("miRNAs") altered after a concussion, mTBI, sTBI, or other TBI, and
   selecting a subject at risk of having a concussion, mTBI, sTBI, or other TBI when said miRNAs are present in an amount significantly below or above that detected in a control; and
   wherein when the subject is an exercising subject, then said detecting comprises detecting a level of at least one miRNA that is distinguishable from that of a control exercising subject not having a concussion or TBI.
2. The method of embodiment 1, further comprising when an altered level is detected, further evaluating the patient for other symptoms of concussion, mTBI, sTBI, or other TBI or treating the subject for concussion, mTBI, sTBI, or other TBI;
3. The method of embodiment 1, wherein said detecting in saliva determines a concentration of at least one miRNA that is not altered in response to exercise or that is altered to a greater extent in concussion, mTIB, sTBI or other TBI compared to its post-exercise level.
4. The method of embodiment 1, wherein said miRNA is not miR-200b-3p or miR-30e-5p.
5. The method of embodiment 1, wherein at least 2, 3, 4, 5, 6, 7, 8, 9, 10, 20 or 50 miRNAs are detected.
6. The method of embodiment 1, wherein the control corresponds to at least one salivary miRNA level of the same subject prior to exposure to a risk of having concussion, mTBI or TBI, or corresponds to at least one miRNA levels of one or more normal subject(s) not having concussion, mTBI or TBI.
7. The method of embodiment 1, wherein the control is a person of the same sex and age, as the subject.
8. The method of embodiment 1, wherein the control is a person of a similar weight, medical, or genetic background as the subject.
9. The method of embodiment 1, wherein the subject is at risk of a concussion, mTBI, sTBI, or other TBI from mixed martial arts, boxing, wrestling, savate, kickboxing, muay thai, sanda, tae kwon do, judo, brazilian jiu-jitsu, sambo, fencing, or other combat sport.
10. The method of embodiment 1, wherein the subject is at risk of a concussion mTBI, sTBI, or other TBI from a non-combat support selected from the group of football, flag football, soccer, rugby, lacrosse, basketball, tennis, equine sports, diving, skydiving, climbing, cycling, vehicular sports such as car racing, or other non-combat sport.
11. The method of embodiment 1, wherein the subject is at risk of a concussion, mTBI, sTBI, or other TBI from construction, excavation, mining, lumberjacking, agriculture, work on an oil rig, firefighting, security, soldiering, or other occupational or physical labor.
12. A composition comprising probes and or primers that identify a level of at least one miRNA in saliva altered after concussion, mTBI, sTBI, or other TBI, that is distinguishable from that of a control exercising subject not having a concussion , mTBI, sTBI, or other TBI.
13. The composition of embodiment 12, wherein the probes and/or primers identify at least 2, 3, 4, 5, 6, 7, 8, 9, 10, 15, 20, 50 more miRNAs altered after concussion, mTBI, sTBI, or other TBI.
14. The composition of embodiment 12 that is a microarray, biochip or chip.
15. A system for detecting miRNA in saliva comprising a microarray containing probes or primers that collectively recognize multiple miRNAs altered after concussion, mTBI, sTBI, or other TBI, and optionally signal transmission, information processing, and data display or output elements.
16. The system of embodiment 15, further comprising one or more elements for receiving, and optionally purifying or isolating miRNA from saliva.
17. A composition comprising one or more miRNAs that are deficient in subject having a concussion, mTBI, sTBI, or other TBI in a form suitable for administration to the subject; and/or a composition comprising one or more agents that lower or inactivate one or more miRNAs elevated in a subject having a concussion, mTBI or TBI.
18. A method for treating a concussion, mTBI or TBI comprising administering the composition of embodiment 17 to a subject in need thereof.
19. A method for selecting a health, weight loss, sports training, exercise regimen, or exercise or injury recovery regimen for a subject comprising:
    detecting in saliva a level of at least one miRNA that is altered after exercise compared to a resting or pre-exercise level, and
    selecting a health, weight loss, sports training, exercise regimen, or exercise or injury recovery regimen for the subject that induces or maintains at least a degree of said altered post-exercise miRNA level in saliva compared to a resting subject or to a control subject or value.
20. The method of embodiment 19, wherein the detecting detects at least 2, 3, 4, 5, 6, 7, 8, 9, 10, 15, 20, 50 more miRNAs altered after exercise.
21. The method of embodiment 19, wherein selecting the health, weight loss, sports training, exercise regimen, or exercise or injury recovery regimen is based on a score based on an average or weighted average score of the alteration of each of the one or more miRNA.
22. The method of embodiment 19, further comprising determining miRNA levels in saliva prior to exercise, exercising the subject, and determining miRNA levels post-exercise.
23. The method of embodiment 19, further comprising determining miRNA levels in saliva prior to exercise, exercising the subject for at least 5, 10, 20, 30, 40, 50, 60, 90 or 120 minutes, and determining miRNA levels post-exercise, wherein said exercise is jogging, running, or another aerobic exercise.
24. The method of embodiment 19, wherein the control subject is the same subject prior to exercise.
25. The method of embodiment 19, wherein the control is based on values for one or more non-conditioned or non-exercising subjects.
26. The method of embodiment 19, wherein the subject is a conditioned or routinely exercising subject and wherein selecting the health, weight loss, sports training, exercise regimen, or exercise or injury recovery regimen is based on maintaining altered miRNA levels compared to non-conditioned or non-exercising subject(s).

27. The method of embodiment 19, wherein selecting a health, weight loss, sports training, exercise regimen, or exercise or injury recovery regimen is based on maintaining one or more miRNA alterations associated with exercise at a level of at least ±1, 2, 5, 10, 20, 50, 100, 200, or 500% of the post-exercise level.
28. The method of embodiment 19, wherein the exercise is running, jogging, or walking.
29. The method of embodiment 19, wherein the exercise comprises skating, skiing, cycling, rowing, weightlifting, boxing, martial arts, hiking, calisthenics, gymnastics, aerobics, yoga, dancing, tennis, racket ball, squash, golf, swimming, horseback riding, rodeo, climbing, or another non-running aerobic exercise.
30. The method of embodiment 19, wherein the exercise comprises soccer, football, basketball, hockey, baseball, or another team sport.
31. The method of embodiment 19, wherein the exercise comprises construction, excavation, mining, lumberjacking, agriculture, work on an oil rig, firefighting, security, soldiering, or other occupational or physical labor.
32. The method of embodiment 19, wherein a level of one or more miRNAs associated with exercising are significantly changed pre- and post-run and has a false discovery rate or FDR <0.05.
33. The method of embodiment 19,
wherein said one or more miRNAs comprise at least one miR-3671, or miR-5095 (down-regulated post-run) and wherein said selecting induces down-regulation of a concentration of at least one of these miRNAs in saliva; or
wherein said one or more miRNAs comprise at least one of miR-7154-3p, miR-200b-5p, miR-5582-3p, miR-6859-3p, miR-6751-5p, or miR-4419a (up-regulated post-run) and wherein said selecting induces up regulation of a concentration of at least one of these miRNAs in saliva.
34. The method of embodiment 19, wherein said one or more miRNAs comprise at least one of hsa-miR-6731-5p, hsa-miR-552-5p, hsa-miR-4675, hsa-miR-6715b-3p, hsa-miR-7852-3p, hsa-miR-19'7-5p, hsa-miR-4428, hsa-miR-6808-3p, hsa-miR-5585-3p, hsa-miR-3972, hsa-miR-186-3p, hsa-miR-6859-2-5p, hsa-miR-6739-5p, hsa-miR-4735-5p, hsa-miR-5095, hsa-miR-3671, hsa-miR-6745, or hsa-miR-6746-3p and wherein said selecting comprises selecting a sex- or gender-specific health, weight loss, sports training, exercise regimen, or exercise or injury recovery regimen for the subject that induces or maintains at least a degree of said altered miRNA level.
35. A composition comprising probes and or primers that identify at least one miRNA in saliva altered after exercising.
36. The composition of embodiment 35, wherein the probes or primers identify at least one miRNA selected from the group consisting of miR-7154-3p, miR-200b-5p, miR5582-3p, miR6859-3p, miR6751-5p, miR4419, miR-3671 and miR-5095 (or other miRNAs whose concentrations change with exercise such as those described by Supplemental Table 2).
37. The composition of embodiment 35, wherein the probes and/or primers identify at least 2, 3, 4, 5, 6, 7, 8, 9, 10, 15, 20, 50 more miRNAs altered after exercising.
38. The composition of embodiment 35 that is a microarray, biochip or chip.
39. A system for detecting miRNA in saliva comprising a microarray containing probes or primers that collective recognize multiple miRNAs altered after exercising, and optionally signal transmission, information processing, and data display or output elements.
40. The system of embodiment 39, further comprising one or more elements for receiving, and optionally purifying or isolating miRNA.
41. A composition comprising one or more miRNAs that is/are deficient in a non-exercising or pre-exercised subject in a form suitable for administration to the subject; and/or a composition comprising one or more agents that lower or inactivate one or more miRNAs elevated in a non-exercising or pre-exercised subject.
42. A method for inducing one or more effects of exercising comprising administering the composition of embodiment 41 to a subject in need thereof.
43. A method for monitoring metabolic status of a subject comprising:
detecting in saliva amounts of one or more miRNAs altered after exercise and associated with metabolic status; and
selecting a health, weight loss, sports training, exercise regimen, or exercise or injury recovery regimen that maintains one or more miRNA levels associated with cardiovascular status at an altered level characteristic of post-exercise levels (e.g., between a resting or non-exercise level and a lower or higher post-exercise level, or at a lower or higher level exceeding the altered post-exercise level).
44. The method of embodiment 43, wherein the subject is a non-conditioned or sedentary subject.
45. The method of embodiment 43, wherein the subject is a conditioned or non-sedentary subject.
46. The method of embodiment 43 comprising monitoring glycerophospholipid metabolism by detecting miRNAs associated with altered glycerophospholipid metabolism.
47. A method for monitoring cardiovascular status of a subject comprising:
detecting in saliva amounts of one or more miRNAs altered after exercise and associated with cardiovascular status; and
selecting a health, weight loss, sports training, exercise regimen, or exercise or injury recovery regimen that maintains one or more miRNA levels associated with cardiovascular status at an altered level characteristic of post-exercise level (e.g., between a resting or non-exercise level and a lower or higher post-exercise level, or at a lower or higher level exceeding the altered post-exercise level).
48. The method of embodiment 47, wherein the subject is a non-conditioned or sedentary subject.
49. The method of embodiment 47, wherein the subject is a conditioned or non-sedentary subject.
50. The method of embodiment 47 comprising monitoring cardiovascular status by detecting miRNAs associated with arrhythmogenic ventricular cardiomyopathy or other cardiomyopathy or arrhythmias.
51. A method for monitoring fluid balance in a subject comprising:
detecting in saliva amounts of one or more miRNAs altered after exercise and associated with fluid balance; and
selecting a health, weight loss, sports training, exercise regimen, or exercise or injury recovery regimen that maintains one or more miRNA levels associated with fluid balance at an altered level characteristic of post-exercise level (e.g., between a resting or non-exercise level and a lower or higher post-exercise level, or at a lower or higher level exceeding the altered post-exercise level).
52. The method of embodiment 51, wherein the subject is a non-conditioned or sedentary subject.
53. The method of embodiment 51, wherein the subject is a conditioned or non-sedentary subject.
54. The method of embodiment 51 that comprises monitoring aldosterone-regulated sodium reabsorption by detecting miRNAs associated with altered aldosterone levels or altered sodium reabsorption.
55. A method for monitoring one or more brain-related biochemical pathways or responses in a subject comprising:
detecting in saliva amounts of one or more miRNAs altered after exercise and associated with said pathways or responses; and
selecting a therapeutic, health, weight loss, sports training, exercise regimen, or exercise or injury recovery regimen that maintains one or more miRNA levels associated with said pathways or responses at an altered level characteristic of post-exercise level (e.g., between a resting or non-exercise level and a lower or higher post-exercise level, or at a lower or higher level exceeding the altered post-exercise level), at a resting level, or at a control level characteristic of a normal resting or exercising subject.
56. The method of embodiment 55, wherein the subject is a non-conditioned or sedentary subject.
57. The method of embodiment 55, wherein the subject is a conditioned or non-sedentary subject.
58. The method of embodiment 55 that comprises monitoring Wnt signaling, morphine addiction, GABAergic synapse response, and/or prolactin signaling.
59. A method for endurance training comprising monitoring one or more miRNAs positively correlated with endurance status and selecting an endurance training routine that maintains or increases the levels of said one or more miRNAs in saliva; and/or monitoring one or more miRNAs negatively-correlated with endurance status and selecting an endurance training routine that reduces the levels of said one or more miRNAs in saliva.
60. The method of embodiment 59, further comprising monitoring the levels of one or more miRNAs in saliva positively-correlated with concussion, mTBI, sTBI, or other TBI and selecting an endurance training routine that maintains or reduces the levels of said miRNAs; and/or further comprising monitoring the levels of one or more miRNAs in saliva negatively-correlated with concussion, mTBI, sTBI, or other TBI and selecting an endurance training routine that maintains or increases the levels of said miRNAs.
61. A method for tracking therapeutic recovery from concussion, mTBI, sTBI or other TBI comprising detecting a concentration of miR-200b-3p and/or miR-30e-5p compared to a pre-injury or normal control value.
62. The method of embodiment 61, further comprising selecting an injury recovery regimen alters the concentrations of miR-200b-3p and/or miR-30e-5p toward the pre-injury or control levels of miR-200b-3p and/or miR-30e-5p.
63. A method for determining or monitoring physical exertion or aerobic performance comprising detecting at least one miRNA described in Supplemental Table 2, an optionally selecting a therapeutic, health, weight loss, sports training, exercise regimen, or exercise or injury recovery regimen that alters a level of at least one of said miRNAs toward a post-exercise level of said miRNA.

Terminology

The materials, methods, and examples are illustrative only and are not intended to be limiting, unless otherwise specified. Numerous modification and variations on the present invention are possible in light of the above teachings. It is therefore to be understood that within the scope of the appended claims, the invention may be practiced otherwise than as specifically described herein.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears. The name, structures, sequences and other characteristics of miRNAs or mRNA target genes described in the references herein, including the related applications described on page 1 of this application, and their correlations to concussion, mTBI, sTBI and other TBIs as well as to exercise or other described pathways or other biochemical phenomena, are specifically incorporated by reference to these publications or patent applications.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:
1. A method for selecting an injury recovery exercise regimen for a subject having a concussion or traumatic brain injury (TBI) comprising:
detecting pre-exercise levels of miR-7154-3p, miR-200b-5p, miR-5582-3p, miR-6859-3p, miR-6751-5p, and miR-4419a in a saliva sample obtained from the subject having the concussion or TBI,
administering an injury recovery exercise regimen to said subject, detecting post-exercise levels of miR-7154-3p, miR-200b-5p, miR-5582-3p, miR-6859-3p, miR-6751-5p, and miR-4419a in a saliva sample obtained from the subject;

selecting the injury recovery regimen for said subject when the post-exercise levels of miR-7154-3p, miR-200b-5p, miR-5582-3p, miR-6859-3p, miR-6751-5p, and miR-4419a are increased in comparison to the pre-exercise levels of miR-7154-3p, miR-200b-5p, miR-5582-3p, miR-6859-3p, miR-6751-5p, and miR-4419a; and continuing to administer the selected injury recovery exercise regimen to said subject.

2. The method of claim 1, further comprising detecting pre-exercise levels of miR-3671 and/or miR-5095 in the saliva sample obtained from the subject and detecting post exercise levels of miR-3671 and/or miR-5095 in the saliva sample obtained from the subject.

3. The method of claim 1, wherein the subject has had a concussion.

4. The method of claim 1, wherein the subject has had a TBI.

5. The method of claim 1, wherein the regimen comprises aerobic exercise.

6. The method of claim 1, wherein the regimen comprises jogging or running.

7. The method of claim 1, wherein the regimen comprises a sports training regimen.

8. The method of claim 1, wherein the regimen further comprises a health or weight loss regimen.

* * * * *